United States Patent
Swinkels

(10) Patent No.: US 11,917,962 B2
(45) Date of Patent: Mar. 5, 2024

(54) CUCUMBER VARIETY NUN 09103 CUL COMPRISING FRUITS WITH A SMALL SEED CAVITY AND/OR INCREASED DRY MATTER CONTENT

(71) Applicant: NUNHEMS B.V., Nunhem (NL)

(72) Inventor: Robert Swinkels, Nunhem (NL)

(73) Assignee: Nunhems B.V., Nunhem (NL)

( * ) Notice: Subject to any disclaimer, the term of this patent is extended or adjusted under 35 U.S.C. 154(b) by 150 days.

(21) Appl. No.: 17/155,915

(22) Filed: Jan. 22, 2021

(65) Prior Publication Data

US 2021/0137044 A1    May 13, 2021

Related U.S. Application Data

(60) Provisional application No. 62/967,955, filed on Jan. 30, 2020.

(51) Int. Cl.
*A01H 6/34* (2018.01)
*A01H 5/08* (2018.01)

(52) U.S. Cl.
CPC ............ *A01H 6/346* (2018.05); *A01H 5/08* (2013.01)

(58) Field of Classification Search
None
See application file for complete search history.

(56) References Cited

U.S. PATENT DOCUMENTS

| | | | | |
|---|---|---|---|---|
| 8,158,860 | B2 * | 4/2012 | Shetty | A01H 6/346 800/278 |
| 8,710,303 | B2 | 4/2014 | Crienen et al. | |
| 10,064,352 | B2 * | 9/2018 | Suelmann | A01H 6/346 |
| 2014/0317769 | A1 * | 10/2014 | Suelmann | A01H 6/346 800/300 |
| 2014/0356514 | A1 * | 12/2014 | Suelmann | A01H 6/346 800/300 |
| 2015/0181824 | A1 * | 7/2015 | Suelmann | A01H 6/346 800/300 |
| 2015/0245570 | A1 | 9/2015 | Vogelaar et al. | |
| 2017/0127631 | A1 * | 5/2017 | Shetty | A01H 6/346 |
| 2018/0054990 | A1 | 3/2018 | Haaring et al. | |

FOREIGN PATENT DOCUMENTS

| | | |
|---|---|---|
| WO | 2009059777 A1 | 5/2009 |
| WO | 2014076249 A1 | 5/2014 |
| WO | 2016207432 A1 | 12/2016 |

OTHER PUBLICATIONS

Parkash et al, 2021, Plant Stress https://doi.org/10.1016/j.stress. 2021.100004.*
Serce et al, 1997, Cucurbit Genet. Coop, https://cucurbit.info/1997/effects-of-water-stress-on-fruit-quality-in-cucumber/.*
Rijk Zwaan (2019, Cucumber High tech Assortment 2019-2020, Rijk Zwaan Dsitribution B.V. The Netherlands.*
"Protocol for Tests on Distinctness, Uniformity And Stability—*Cucumis sativus* L., Cucumber and Gherkin", UPOV Code: CUCUM_SAT, Community Plant Variety Office, CPVO-TP/061/2 Rev.2, Mar. 19, 2019, pp. 1-34.
"United States Standards for Grades of Cucumbers", US Department of Agriculture, Jan. 23, 2018, pp. 1-11.
"Guidelines for the conduct of tests for Distinctness, Uniformity and Stability—Cucumber, Gherkin, UPOV Code: CUCUM_SAT, *Cucumis sativus* L.", UPOV, International Union for the Protection of New Varieties of Plants, Geneva, TG/61/7, correction 2, Mar. 13, 2019, pp. 1-48.
Objective description of Variety: Cucumber (*Cucumis sativus* L.), US Department of Agriculture, Agricultural Marketing Service, Science and Technology, Plant Variety Protection Office, Exhibit C, Jun. 2015, pp. 1-3.
Guan, et al., "Parthenocarpic cucumber cultivar evaluation in high-tunnel production", HortTechnology, vol. 29, Issue 5, Oct. 2019, pp. 634-642.
Henikoff, et al., "Amino acid substitution matrices from protein blocks", Proceedings of the National Academy of Sciences of the United States of America, vol. 89, Issue 22, Nov. 15, 1992, pp. 10915-10919.
Huang, et al., "The genome of the cucumber, *Cucumis sativus* L.", Nature Genetics, vol. 41, Issue 12, Nov. 1, 2009, pp. 1275-1283.
Qi, et al., "A genomic variation map provides insights into the genetic basis of cucumber domestication and diversity", Nature Genetics, vol. 45, Issue 12, Oct. 20, 2013, pp. 1510-1518.

* cited by examiner

*Primary Examiner* — Anne Kubelik
(74) *Attorney, Agent, or Firm* — ArentFox Schiff LLP

(57) ABSTRACT

The disclosure relates to cucumber plants producing fruits comprising a small seed cavity and/or an increased dry matter content, and to methods for generating such plants, and their use.

24 Claims, 6 Drawing Sheets

Figure 4 (Packaged + 6 days)
NUN09103CUL
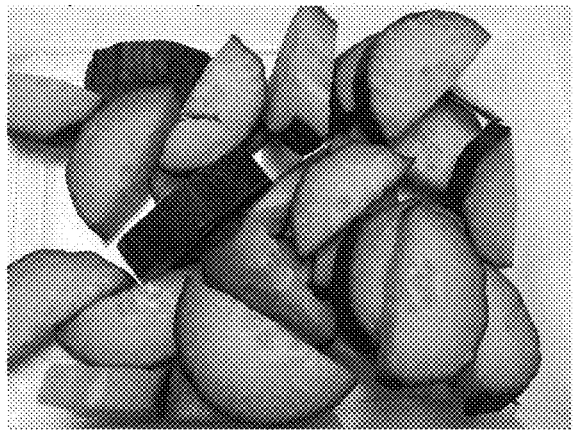
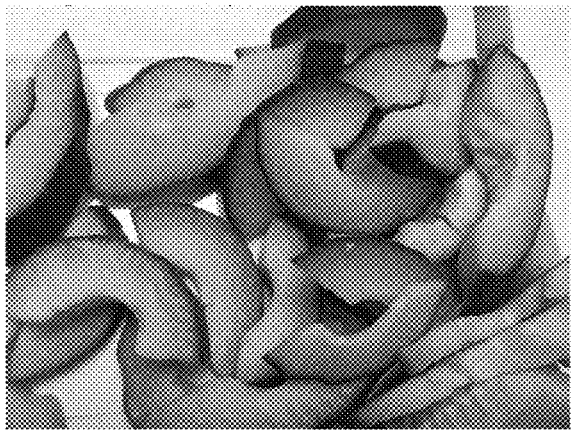
Hi Power
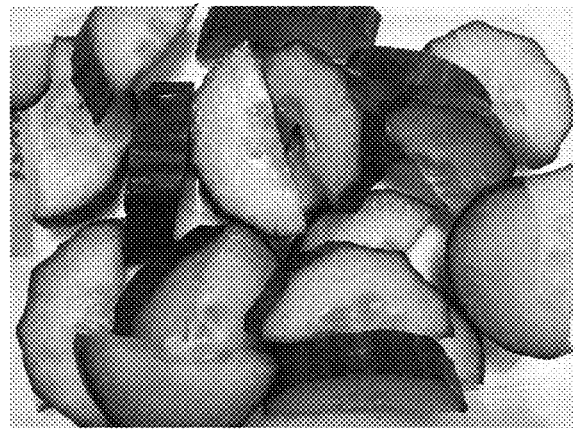
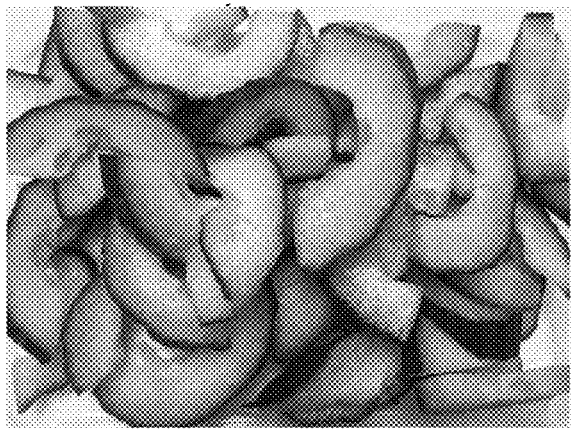

CUCUMBER VARIETY NUN 09103 CUL COMPRISING FRUITS WITH A SMALL SEED CAVITY AND/OR INCREASED DRY MATTER CONTENT

CROSS-REFERENCE TO RELATED APPLICATION

This application claims priority to the U.S. Provisional Application No. 62/967,955, filed on Jan. 30, 2020, which is hereby incorporated by reference in its entirety.

FIELD OF THE DISCLOSURE

The disclosure relates to cucumber variety NUN 09103 CUL. The disclosure further relates to vegetative reproductions of cucumber variety NUN 09103 CUL, methods for tissue culture of cucumber variety NUN 09103 CUL and regenerating a plant from such a tissue culture and to phenotypic variants of cucumber variety NUN 09103 CUL. The disclosure also relates to progeny of cucumber variety NUN 09103 CUL and the hybrid varieties obtained by crossing the cucumber variety NUN 09103 CUL as a parent line with plants of other varieties or parent lines.

BACKGROUND OF THE DISCLOSURE

Cultivated cucumber (*Cucumis sativus* var. *sativus* L.) is an important vegetable crop worldwide. It belongs to the family *Cucurbitaceae*. It is thought to originate from South East Asia from wild ancestors with small, bitter fruits, such as *Cucumis sativus* var. *hardwickii*.

The cultivated cucumber genome has seven pairs of chromosomes (n=7) and a haploid genome size of about 367 Mb (Megabases) with an estimated total of about 26,682 genes. The cucumber genome was the first vegetable genome to be sequenced (Huang et al. 2009, Nature Genetics, Volume 41, Number 12, p1275-1283, and the world wide web at //cucurbitgenomics.org/).

Long cucumbers are generally cultivated in the glasshouse, either in the traditional Umbrella or T-system or in the high-wire cultivation system. The fruits are mainly sold fresh, as whole fruits, but there is an increasing need for processed fruits, such as slices or dices, to be included in salads or on sandwiches and the like. Processed cucumber fruits are however quite moist and leak moisture from the cut surfaces over time. This reduces the shelf-life of the cut pieces and of the food product comprising these. It also increases the risk of bacterial contamination and reduces the taste. Sometimes moisture binders are applied to counteract the leakage and thereby increase the shelf life of the product, or the seed cavity is removed from the fruits and only the fruit flesh (mesocarp) is used. The large seed cavity also makes cutting more difficult during processing.

One variety has been developed, Consapino RZ F1, which has a reduced seed cavity size, whereby as a result of the reduced seed cavity size, the cut cucumbers also leak less moisture. The reduced seed cavity size is described to be seen in seeds comprising two QTLs together, one on chromosome 1 and one on chromosome 2, and the trait was only seen in cucumber plants which are parthenocarpic (capable of parthenocarpic fruit set). The donor of the QTLs is described to 'a combination of genotypes' of seeded, non-parthenocarpic cucumbers. See WO2016/207432, page 3 (first paragraph). This limits the use of the QTLs to parthenocarpic cucumbers. Further, no QTLs for conferring reduced moisture content or leakage are disclosed.

SUMMARY OF THE VARIOUS ASPECTS OF THE DISCLOSURE

There is need to reduce the moisture leakage and/or reduce the size of the seed cavity of cucumber fruits. Moreover, there is a need for other sources of QTLs conferring a smaller seed cavity size, which are not limited in their use to parthenocarpic cucumbers. There is also a need for QTLs which confer an increase in dry matter content (reduced moisture leakage and/or reduced moisture content) of cucumber fruits, e.g., which can be used without reducing the seed cavity size or alternatively with reducing seed cavity size. The present disclosure addresses these and other needs.

The present disclosure relates to the field of cucumber breeding. Provided is an introgression of one or more Quantitative Trait Loci (QTLs) in cultivated cucumbers (*Cucumis sativus* var. *sativus*) which, when present in long cucumber, confer an increase in dry matter (reduced moisture leakage and/or reduced moisture content) of the cucumber fruits and/or a smaller seed cavity than long cucumber types lacking the QTLs.

Surprisingly, an in-house short cucumber line was found which, when used in backcrossing with long cucumber, resulted in the long cucumber fruits having an increase in dry matter (reduced moisture leakage and/or reduced moisture content) of the cucumber fruits and a smaller seed cavity of the fruits. The short, parthenocarpic cucumber line itself (the donor) did not show this phenotype and it was, therefore, a surprise that the long cucumber did show this phenotype.

Without wishing to be bound, initial mapping studies in a BC1S1 population (in which the small seed cavity trait and the dry matter trait segregated) indicate that one or more QTLs are involved, which confer the increase in dry matter and one or more QTLs are involved which confer the reduction of the seed cavity size. One or more of these QTLs may also have an effect on both seed cavity size and dry matter of the fruits. The short, parthenocarpic cucumber line is herein referred to as the donor of the small seed cavity (and of the underlying one or more QTLs) and/or of the increase in dry matter (and of the underlying one or more QTLs).

Through backcrossing and selfing, a long cucumber line comprising the donor QTLs has been developed. From this line, a double haploid line was made which showed the small seed cavity and dry matter traits. This double haploid (DH) line was crossed to an elite long cucumber line lacking the donor QTLs, to obtain an F1 hybrid. This F1 hybrid variety is named NUN 09103 CUL. This F1 hybrid therefore contains a haploid genome (the chromosomes from the DH line) in which the genetic elements of the short cucumber donor are present which result in the fruits having an increased dry matter content and/or a smaller seed cavity compared to a control plant lacking the genetic elements, such as the long cucumber variety Hi Power (NUN 29997 CUL).

A representative sample of seeds of cucumber variety NUN 09103 CUL comprising the QTLs from the donor has been deposited under accession number NCIMB 43517, and from the deposit, or from ascendants or descendants of this deposit, the QTLs conferring an increase in dry matter (reduced moisture leakage and/or reduced moisture content)

and/or small seed cavity can be easily transferred into any other cucumber type, especially other long cucumber types.

Phenotypic selection can be used to transfer the small seed cavity (and of the underlying one or more QTLs) and/or of the increase in dry matter (and of the underlying one or more QTLs) from the deposited seeds into other cucumbers.

BRIEF DESCRIPTION OF DRAWINGS

FIG. 4 shows photos of cut fruit pieces of cucumber variety NUN 09103 CUL and Hi Power after packaging in foil and 6 days of storage at 6° C. The left panel shows pieces where the seed cavity has not been removed and the right panel shows the pieces where the fruit cavity has been removed.

GENERAL DEFINITIONS

Figure 1:
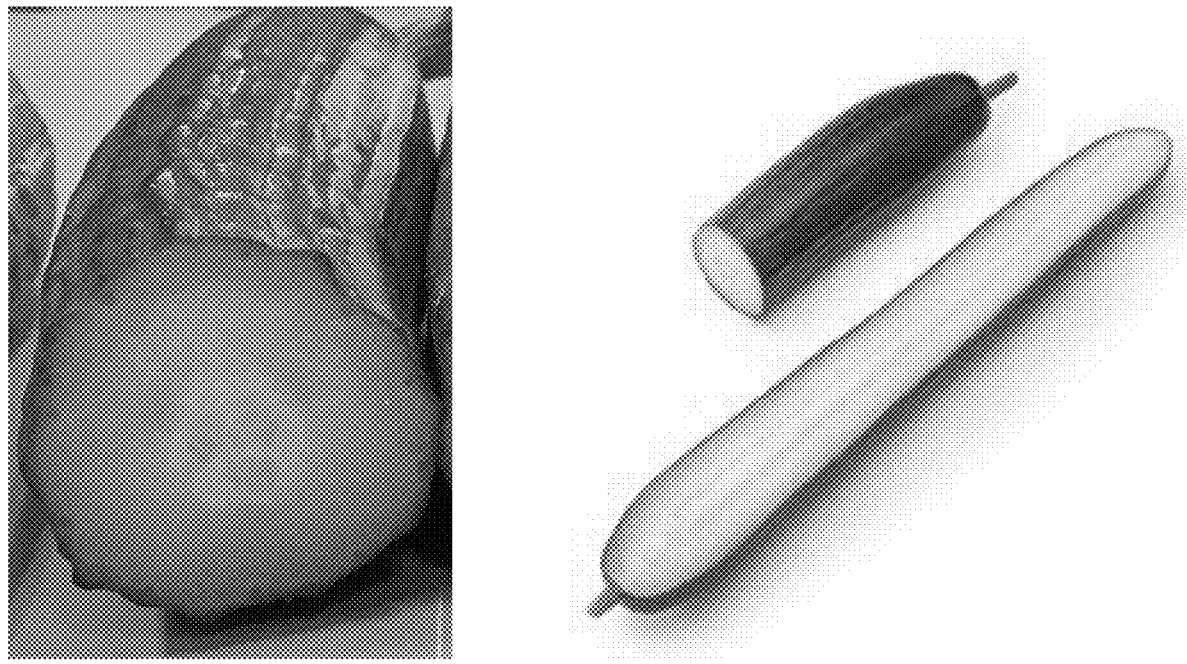
FIG. 1 shows fruit of cucumber variety NUN 09103 CUL. The traverse section shows the seed cavity, also referred to as 'fruit cavity' herein (or core) in the center of the fruit (also referred to as endocarp), surrounded by fruit flesh layer (mesocarp).

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested cucumber fruits or parts thereof), flowers, leaves, seeds, tubers, bulbs, clonally propagated plants, roots, rootstocks, stems, root tips and the like. Also any developmental stage is included, such as seedlings, immature and mature, etc. When "seeds of a plant" are referred to, these either refer to seeds from which the plant can be grown or to seeds produced on the plant, after self-fertilization or cross-fertilization.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes. Thus a plant defined only by the presence of a QTL is not a plant variety, as thousands of other genes which define a plant variety are undefined and a plant defined only by the presence of a QTL (or 2 or 3 QTLs) is not uniform and stable for these thousands of genes and the characteristics conferred by these genes. A QTL can be used to develop many different plant varieties, e.g., a different long cucumber variety than NUN 09103 CUL, or a slicer variety, which is uniform and stable for all its physiological and morphological characteristics such as leaf size or shape, leaf color, fruit size and color, warts, bitterness, plant height, etc. and which also comprises one or more QTLs conferring an increase in dry matter content and/or a reduction in seed cavity size.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g., at least 3, 4, 5, 6, 7 or more) of inbreeding, resulting in a plant line with a high uniformity.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a (genomic) DNA sequence comprising a region (transcribed region), which is transcribed into a messenger RNA molecule (mRNA) in a cell, and an operably linked regulatory region (e.g., a promoter). Different alleles of a gene are thus different alternatives form of the gene, which may be in the form of e.g., differences in one or more nucleotides of the genomic DNA sequence (e.g., in the promoter sequence, the exon sequences, intron sequences, etc.), mRNA and/or amino acid sequence of the encoded protein.

The term "locus" (loci plural) means a specific place or places or a site on a chromosome where for example a QTL, a gene or genetic marker is found. A dry matter locus is, thus, the location in the genome of cucumber, where a QTL which increases the dry matter content of the fruits is found, when the locus is present in long cucumbers. Likewise, a seed cavity locus is, thus, the location in the genome of cucumber, where a QTL which reduces seed cavity size of the fruits is found, when the locus is present in long cucumbers. In cultivated cucumber described herein, the QTLs are found on chromosome of cultivated cucumber (using the chromosome assignment of Huang et al. 2009, Nature Genetics, Volume 41, Number 12, p1275-1283 and world wide web at //cucurbitgenomics.org/organism/2 and described therein as "Cucumber (Chinese Long) v2 Genome") i.e., they are introgressed into the cultivated cucumber genome from a donor cucumber (also referred to as donor herein).

A "quantitative trait locus", or "QTL" is a chromosomal locus that encodes for one or more alleles that affect the expressivity of a continuously distributed (quantitative) phenotype.

"Dry matter QTLs" or "increased dry matter QTLs" refers to an increase in dry matter content of the fruits which is being conferred by one or more QTLs of the donor. "Dry matter content increase" refers to the (average) reduction in moisture leakage and/or moisture content of the fruits of plants comprising the QTLs of the donor, compared to control plants lacking the QTLs, when the plants are grown under the same conditions. An average increase of the dry matter content of the fruits can e.g., be measured by a reduction in moisture leakage from cut pieces of fruits during a defined period of time and under defined conditions (referred to herein as "reduced moisture leakage") and/or a reduction in the amount of moisture released from the cucumber fruits (or parts thereof) when applying a defined pressure to the fruits (or fruit parts, e.g., to the fruit flesh and/or the seed cavity parts) (referred to herein as "reduced moisture content"), or other methods, such as weighing fresh cucumbers or cucumber parts, drying them for a certain period of time and then weighing the dried cucumbers or cucumber parts to determine the dry matter content. For example, 4 representative fruits of a plant comprising the QTLs and 4 representative fruits of a control plant lacking the QTLs (e.g., the recurrent parent, or the genetic control) are harvested at one time point and the average moisture leakage and/or moisture content is determined.

"Dry matter content increase of the fruit flesh" refers to refers to the (average) reduction in moisture leakage and/or moisture content of the fruit flesh (mesocarp) of plants comprising the QTLs of the donor, compared to control plants lacking the QTLs, when the plants are grown under the same conditions.

"Dry matter content increase of the seed cavity" refers to refers to the (average) reduction in moisture leakage and/or moisture content of the seed cavity (endocarp) of plants comprising the QTLs of the donor, compared to control plants lacking the QTLs, when the plants are grown under the same conditions.

Figure 2:
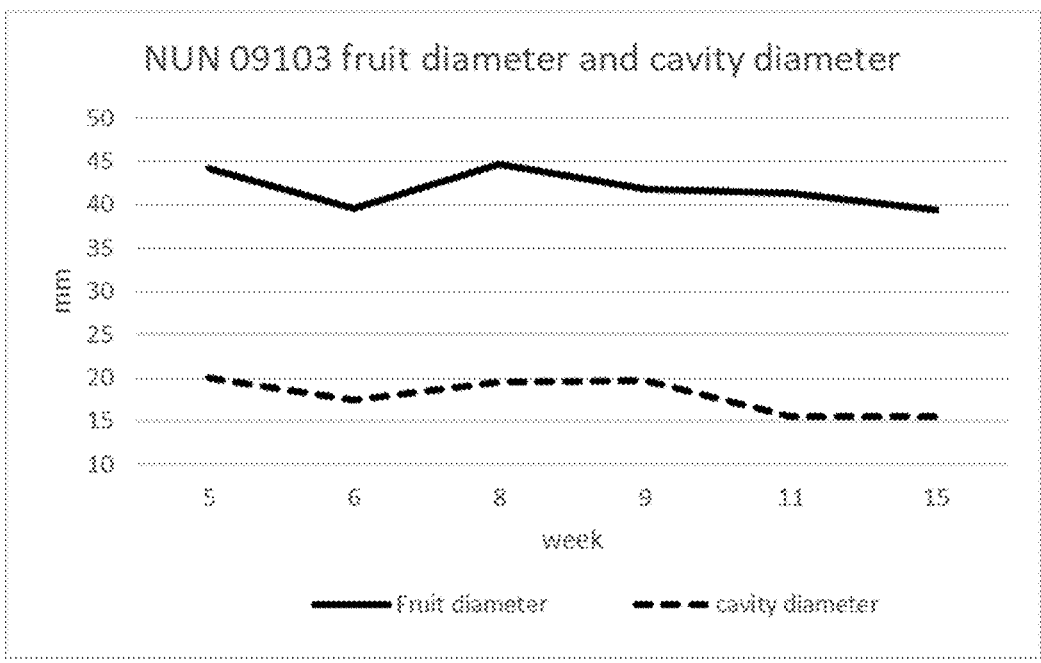
FIGS. 2 shows average fruit diameter and average seed cavity diameter (in mm, on the Y-axis) of four representative harvest stage cucumber fruits harvested from four different plants of NUN 09103CUL at different time points (X-axis, showing weeks of the year, i.e. week 5, 6, 8, 9, 11, and 15 of the year 2019). Week 5 of 2019 was about 4 weeks after planting in the greenhouse. Plants were grown in the high-wire system, together with varieties Consapino RZ and Hi Power.
Figure 3:
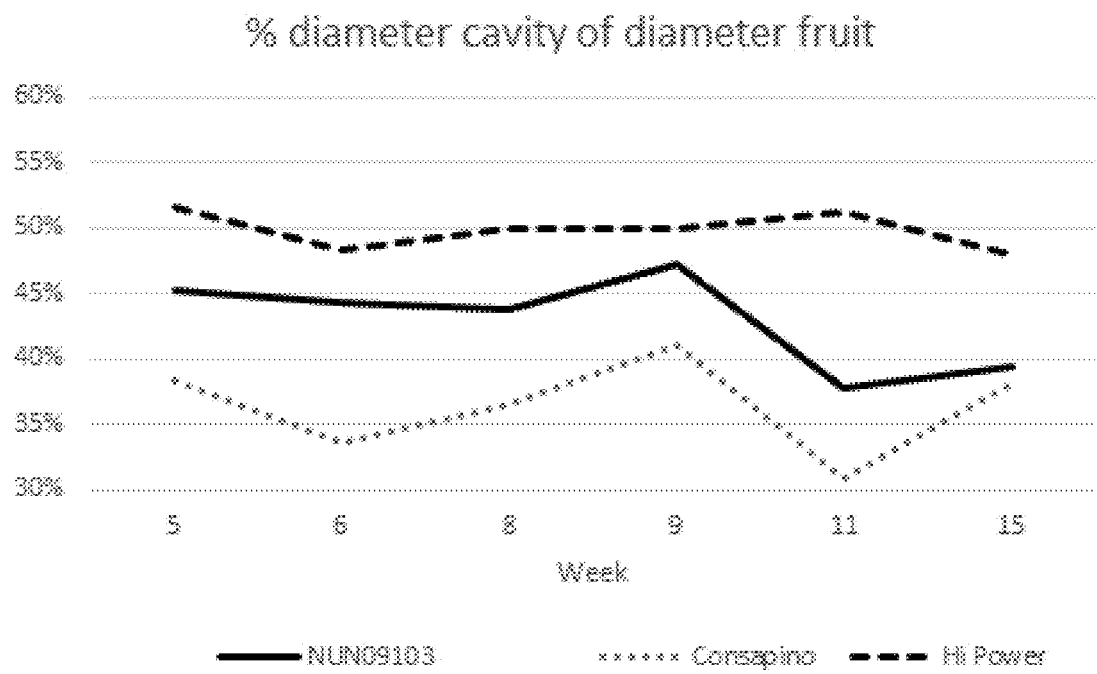
FIG. 3 shows the average seed cavity diameter of cucumber variety NUN 09103CUL, Consapino RZ and Hi Power, expressed as a percentage of the average fruit diameter. As can be seen, Hi-Power has the largest seed cavity diameter (48-52% of the fruit diameter), cucumber variety NUN 09103 CUL has a significantly smaller seed cavity diameter (38-47% of the fruit diameter) and Consapino RZ has an even smaller seed cavity diameter (31-38% of the fruit diameter).
Figure 5:
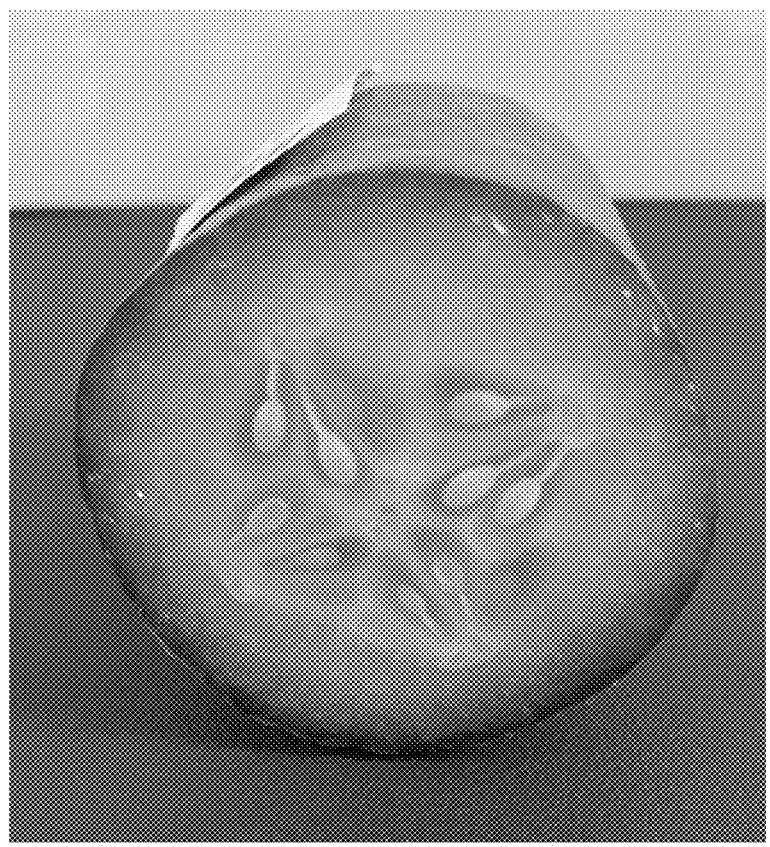
FIG. 5 shows fruit of the donor.
Figure 6:
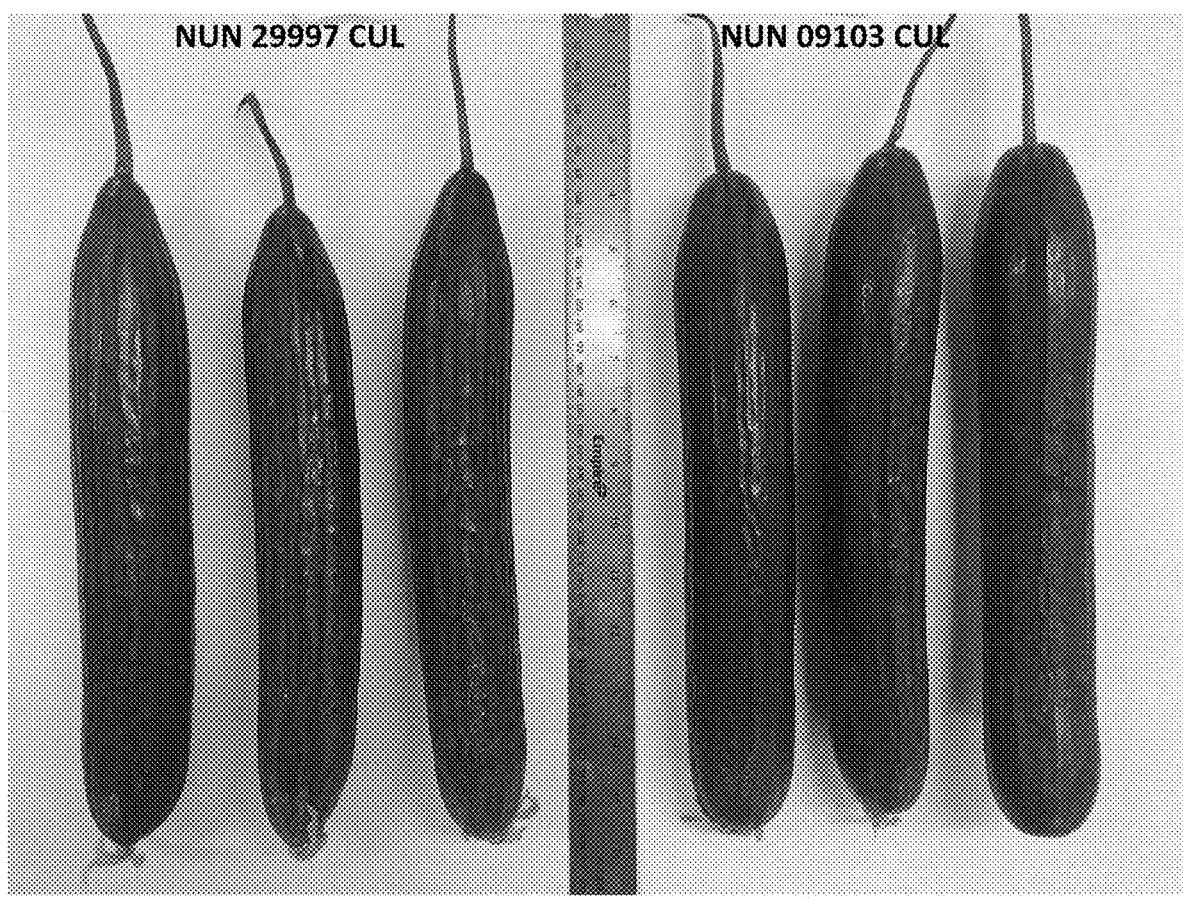
FIG. 6 shows the fruit comparison of cucumber variety NUN 09103 CUL and Hi Power.
Figure 7:
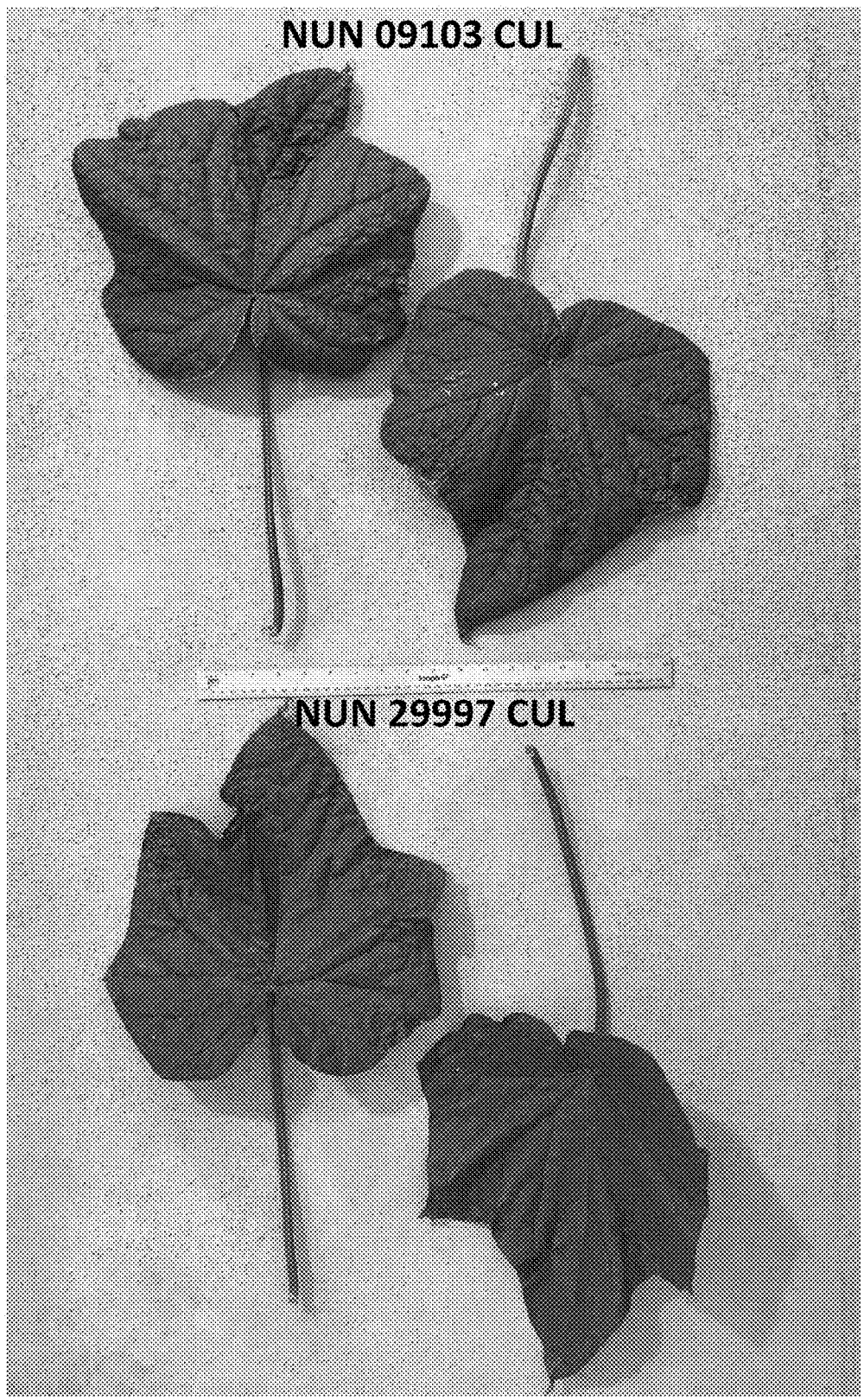
FIG. 7 shows the leaf comparison of cucumber variety NUN 09103 CUL and Hi Power.

"Seed cavity QTLs" or "cavity size QTLs" or "reduced cavity size QTLs" refers to the reduction in seed cavity size of the fruits which is being conferred by one or more QTLs of the donor. "Reduced seed cavity size" or "reduced or smaller cavity size" or "smaller or reduced seed cavity size" refers to the reduction in (average) seed cavity size of the fruits of plants comprising the QTLs of the donor, compared to control plants lacking the QTLs, when the plants are grown under the same conditions. The average seed cavity size of the fruits refers to the diameter of the seed cavity of the fruits relative to the diameter of the fruit itself and the average seed cavity diameter is, therefore, preferably expressed as the percentage of the average fruit diameter. For example, 4 representative fruits of a plant comprises the QTLs and 4 representative fruits of a control plant lacking the QTLs (e.g., the recurrent parent, or the genetic control) are harvested at one time point and the average fruit diameter and cavity diameter is measured for the 4 fruits, see e.g., FIG. 2, showing the average fruit diameter and average cavity diameter for NUN09103CUL, and FIG. 3, showing the same data (solid line) wherein the average seed cavity diameter is expressed as a percentage of the average fruit diameter, e.g., in week 5 the seed cavity diameter is 45% of the overall fruit diameter for cucumber variety NUN 09103 CUL comprising the QTLs from the donor, while the seed cavity diameter of the control, Hi Power (lacking the QTLs) is 52% of the average fruit diameter.

"Cucumber genome" and "physical position on the cucumber genome" and "chromosomes" refers to the physical genome of cultivated cucumber, world wide web at //cucurbitgenomics.org/ under "Cucumber (Chinese Long) v2 Genome"/, and the physical chromosomes and the physical position on the chromosomes.

"Physical distance" between loci (e.g., between molecular markers and/or between phenotypic markers) on the same chromosome is the actually physical distance expressed in bases or base pairs (bp), kilo bases or kilo base pairs (kb) or megabases or mega base pairs (Mb).

"Genetic distance" between loci (e.g., between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Introgression fragment" or "introgression segment" or "introgression region" refers to a chromosome fragment (or chromosome part or region) which has been introduced into another plant of the same or related species by crossing or traditional breeding techniques, such as backcrossing, i.e., the introgressed fragment is the result of breeding methods referred to by the verb "to introgress" (such as backcrossing). In cucumber, a donor cucumber (e.g., seeds of cucumber variety NUN 09103 CUL, or progeny or ancestors thereof) can be used to introgress fragments of the donor genome into the genome of cultivated cucumber, *Cucumis sativus* var. *sativus* L, e.g., into long cucumber lines, in order to develop long cucumber varieties with one or more QTLs from the donor. It is understood that the term "introgression fragment" never includes a whole chromosome, but only a part of a chromosome. The introgression fragment can be large, e.g., even three quarter or half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 350,000 bp, 200,000 bp (equals 200 kilo base pairs) or less, about 100,000 bp (100 kb) or less, about 50,000 bp (50 kb) or less, about 25,000 bp (25 kb) or less.

"Cultivated cucumber" or "domesticated cucumber" refers to plants of *Cucumis sativus* var. *sativus* (varieties, breeding lines or cultivars, cultivated by humans and having good agronomic characteristics, especially producing edible and marketable fruits of good size and quality and uniformity); such plants are not "wild cucumber" or "primitive cucumber" plants, i.e., plants which generally have much poorer yields and poorer agronomic characteristics than cultivated plants and are less uniform genetically and in their physiological and/or morphological characteristics. "Wild plants" of "wild cucumber" include, for example, ecotypes, landraces or wild accessions or wild relatives of a species. Cultivated cucumber plants (lines or varieties) can also be distinguished from wild or primitive cucumber accessions by the significantly lower amount of SNPs (less than 2,000,000 SNPs) and INDELs (insertions/deletions of shorter than 5 bp; less than 150,000 INDELs) in the genome and their significantly lower nucleotide diversity (equal to or less than $2.3 \times 10^{-3}$ π), as described in Table 1 of Qi et al, Nature Genetics December 2013, Vol 45, No. 12, pages 1510-1518. SNP numbers, INDEL numbers and nucleotide diversity can be determined as described herein, especially in the section "Online Methods".

"Indian cucumber group" refers to wild or wild relatives of cucumbers from India, having a high amount of SNPs (more than 3,000,000 SNPs) and INDELs (insertions/deletions of shorter than 5bp; more than 200,000 INDELs) in the genome and high nucleotide diversity (more than $3.0 \times 10^{-3}$ π or even more than $4.0 \times 10^{-3}$ π).

"Eurasian cucumber group" refers to cultivated cucumbers from central or western Asia, Europe and the United States, having a low amount of SNPs (less than 2,000,000 SNPs, or less than 1,500,000 SNPs) and INDELs (insertions/deletions of shorter than 5 bp; less than 150,000 INDELs) in the genome and a low nucleotide diversity (equal to or less than $2.3 \times 10^{-3}$ π, preferably less than $2.0 \times 10^{-3}$ π).

"East Asian cucumber group" refers to cultivated cucumbers from East Asia, such as China, Korea and Japan, having a low amount of SNPs (less than 2,000,000 SNPs, or less than 1,500,000 SNPs) and INDELs (insertions/deletions of shorter than 5 bp; less than 150,000 INDELs, preferably less than 100,000) in the genome and a low nucleotide diversity (equal to or less than $2.3 \times 10^{-3}$ π, preferably less than $2.0 \times 10^{-3}$ π or even less than $1.5 \times 10^{-3}$ π).

"Xishuangbanna cucumber group" refers to cucumbers from the Xishuangbanna region of China, having a low amount of SNPs (less than 2,000,000 SNPs, or less than 1,500,000 SNPs or even less than 100,000 SNPs) and INDELs (insertions/deletions of shorter than 5 bp; less than 150,000 INDELs, preferably less than 100,000) in the genome and a low nucleotide diversity (equal to or less than $2.3 \times 10^{-3}$ π, preferably less than $2.0 \times 10^{-3}$ π or even less than $1.5 \times 10^{-3}$ π).

"Wild cucumber" or "primitive cucumber" refers to *C. sativus* var. *sativus* which generally have much poorer yields and poorer agronomic characteristics than cultivated plants and are less uniform genetically and in their physiological and/or morphological characteristics. Wild plants include for example ecotypes, landraces or wild accessions or wild relatives of a species.

"Wild relatives of cucumber" refer to *Cucumis sativus* var. *hardwickii*, *C. sativus* var. *sikkimensis*, *Cucumis sativus* var. *xishuangbannesis*.

"Landrace(s)" refers to primitive cultivars of *Cucumis sativus* var. *sativus* developed in local geographic regions, which often show a high degree of genetic variation in their genome and exhibit a high degree of morphological and/or physiological variation within the landrace (e.g., large variation in fruit size, etc.), i.e., are significantly less uniform than cultivated cucumber. Landraces are, therefore, herein included in the group "wild cucumber", which is distinct from "cultivated cucumber".

"Uniformity" or "uniform" relates to the genetic and phenotypic characteristics of a plant line or variety. Inbred lines are genetically highly uniform as they are produced by several generations of inbreeding. Likewise, and the F1 hybrids which are produced from such inbred lines are highly uniform in their genotypic and phenotypic characteristics and performance.

"SNP marker" refer herein to single nucleotide polymorphisms of a genomic sequence linked to a QTL. This nucleotide, or sequence comprising the nucleotide, is also referred to as the "SNP genotype" or "SNP nucleotide" of the plant or plant part. QTL mapping can be used to identify SNP markers linked to a QTL and which are present on the introgression fragment which comprises the QTL.

The "haplotype" or "haploid genotype" refers to the haploid genotype of several genetic loci in a plant, especially of several SNP markers or several sequences comprising the SNP markers.

A genetic element, an introgression fragment, or a locus (e.g., QTL), a gene or allele conferring a trait (such as internal fruit rot resistance) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus (e.g., the QTL), introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant (or genomic DNA, cell or tissue of a plant) comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like, or combinations of techniques.

"Control plant" is a cultivated cucumber genotype, breeding line, hybrid or variety lacking the QTLs (lacking the introgression fragments from the donor comprising the QTLs). To compare the trait between the control plant and the plant comprising the one or more QTLs, the control plant is from the same type as the plant comprising the one or more QTLs, e.g., the long cucumber type. "Genetic control" is a cultivated cucumber genotype, breeding line, variety or hybrid which has the same or very similar cultivated genome as the cucumber plant comprising the one or more QTLs, except that it lacks the QTLs.

The term "marker assay" refers to a molecular marker assay which can be used to test whether on cultivated *C. sativus* var. *sativus* comprises one or more QTLs from a donor, by detecting the presence of the marker genotypes or haplotypes linked to the QTL.

"Flanking markers" are markers which are on either side of the QTL, i.e., the QTL is located on the chromosomal region in-between the flanking markers.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 4, 5, 6, 7, 8, 9, 10, 15, 20 or more plants (and/or plant parts) are measured, preferably in randomized experimental designs with several replicates and suitable control plants grown under the same conditions in the same experiment. "Statistically significant" or "statistically significantly" different or "significantly" different refers to a characteristic of a plant line or variety that, when compared to a suitable control (e.g., the genetic control) show a statistically significant difference in that characteristic (e.g., the p-value is less than 0.05, p<0.05, using a T-test) from the mean of the control.

A "recombinant chromosome" refers to a chromosome having a new genetic makeup arising through crossing-over between homologous chromosomes. Herein, for example, one or more recombinant cucumber chromosomes are provided comprising an introgression from a donor cucumber, which comprise a QTL that increases dry matter content of the fruits and/or reduces seed cavity size of the fruits.

"Epistasis" refers to the interaction between genes or loci.

The term "traditional breeding techniques" encompasses herein crossing, backcrossing, selfing, selection, double haploid production, embryo rescue, protoplast fusion, marker assisted selection, mutation breeding etc., all as known to the breeder (i.e., methods other than genetic modification/transformation/transgenic methods), by which, for example, a recombinant chromosome comprising a QTL from a donor can be obtained, identified and/or transferred.

"Backcrossing" refers to a breeding method by which a (single) trait, such as a QTL, can be transferred from a (generally inferior) genetic background (also referred to as "donor") into a different (generally superior) genetic background (also referred to as "recurrent parent"). An offspring of a cross (e.g., an F1 plant obtained by crossing a donor with a cultivated cucumber; or an F2 plant or F3 plant, etc., obtained from selfing the F1) is "backcrossed" to the parent with the different (generally superior) genetic background, e.g., to the cultivated parent. After repeated backcrossing, the trait of the first (donor) genetic background will have been incorporated into the different (recipient) genetic background.

"Marker assisted selection" or "MAS" is a process of using the presence of molecular markers, which are genetically and physically linked to a particular locus or to a particular chromosome region (e.g., introgression fragment), to select plants for the presence of the specific locus or region (introgression fragment). For example, a molecular marker genetically and physically linked to a QTL, can be used to detect and/or select cucumber plants comprising the QTL. The closer the genetic linkage of the molecular marker to the locus (e.g., about 7 cM, 6 cM, 5 cM, 4 cM, 3 cM, 2 cM, 1 cM, 0.5 cM or less), the less likely it is that the marker is dissociated from the locus through meiotic recombination. Likewise, the closer two markers are linked to each other (e.g., within 7 cM or 5 cM, 4 cM, 3 cM, 2 cM, 1 cM or less) the less likely it is that the two markers will be separated from one another (and the more likely they will co-segregate as a unit).

A marker "within 7 cM or within 5 cM, 3 cM, 2 cM, or 1 cM" of another marker refers to a marker which genetically maps to within the 7cM or 5cM, 3 cM, 2 cM, or 1 cM region flanking the marker (i.e., either side of the marker). Similarly, a marker within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb, 2 kb, 1 kb or less of another marker refers to a marker which is physically located within the 5 Mb, 3 Mb, 2.5 Mb, 2 Mb, 1 Mb, 0.5 Mb, 0.4 Mb, 0.3Mb, 0.2 Mb, 0.1 Mb, 50 kb, 20 kb, 10 kb, 5 kb, 2 kb, 1 kb or less, of the genomic DNA region flanking the marker (i.e., either side of the marker).

"LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

"Vegetative propagation", "vegetative reproduction" or "clonal propagation" are used interchangeably herein and mean the method of taking part of a plant and allowing that plant part to form at least roots where plant part is, e.g., defined as or derived from (e.g., by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation. In one aspect, propagation by grafting, e.g., a scion onto a rootstock, is included herein.

"Cell culture" or "tissue culture" refers to the in vitro culture of cells or tissues of a plant.

"Regeneration" refers to the development of a plant from cell culture or tissue culture or vegetative propagation.

"Non-propagating cell" refers to a cell which cannot be regenerated into a whole plant.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g., the nucleic acid sequence in a bacterial host cell or in the plant nuclear or plastid genome. When referring to a "sequence" herein, it is understood that the molecule having such a sequence is referred to, e.g., the nucleic acid molecule.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g., minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimizes the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (see, Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (as determined by Emboss "needle" using default parameters, i.e., gap creation penalty =10, gap extension penalty=0.5, using scoring matrix DNA-FULL for nucleic acids an Blosum62 for proteins).

When reference is made to a nucleic acid sequence (e.g., DNA or genomic DNA) having "substantial sequence identity to" a reference sequence or having a sequence identity of at least 80%, e.g., at least 85%, 90%, 95%, 98% or 99% nucleic acid sequence identity to a reference sequence, in one embodiment said nucleotide sequence is considered substantially identical to the given nucleotide sequence and can be identified using stringent hybridization conditions. In another embodiment, the nucleic acid sequence comprises one or more mutations compared to the given nucleotide sequence but still can be identified using stringent hybridization conditions.

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g., 100 nt) are for example those which include at least one wash in 0.2×SSC at 63° C. for 20 min, or equivalent conditions. Stringent conditions for DNA-DNA hybridization (Southern blots using a probe of e.g., 100 nt) are for example those which include at least one wash (usually 2) in 0.2×SSC at a temperature of at least 50° C., usually about 55° C., for 20 min, or equivalent conditions.

"QTL mapping" refers to a well-known method of identifying QTLs on chromosome regions of the genome. "Fine-mapping" refers to methods by which the position of a QTL can be determined more accurately (narrowed down) and by which the size of the introgression fragment comprising the QTL is reduced. For example, Near Isogenic Lines for the QTL (QTL-NILs) can be made, which contain different, overlapping fragments of the introgression fragment within an otherwise uniform genetic background of the recurrent parent. Such lines can then be used to map on which fragment the QTL is located and to identify a line having a shorter introgression fragment comprising the QTL. In this way sub-fragments of the introgression fragments for QTL can be identified which comprises the QTL, but which are shorter than the fragment found in the deposited seeds, and which consequently lack one or more of the SNP markers of the introgression fragment, especially on either side of the fragment.

"Candidate gene" is the gene which is assumed to underlie and to be causal of the trait conferred by the QTL. The candidate gene can be found by fine-mapping and looking at the genes present in the narrowed-down region.

The terms "cucumber plant designated NUN 09103 CUL", "NUN 09103 CUL", "NUN 09103", "NUN 09103 F1", "09103 CUL", "cucumber 09103", or "ROCU 103" are used interchangeably herein and refers to cucumber plant of variety NUN 09103 CUL, a representative seed of which having been deposited under Accession Number NCIMB 43517.

DETAILED DESCRIPTION OF VARIOUS ASPECTS OF THE DISCLOSURE

The present disclosure relates to a cultivated *Cucumis sativus* var. *sativus* plant comprising one or more QTLs, introgressed from a donor cucumber, which confer an increased dry matter content of the fruits (reduced moisture leakage and/or reduced moisture content) and/or which confer a smaller seed cavity compared to a control cucumber plant lacking the QTLs (e.g., the recurrent parent or genetic control).

Surprisingly, an in-house short cultivated cucumber line was found which, when used in backcrossing with long cultivated cucumber, resulted in the long cucumber fruits having an increase in dry matter (reduced moisture leakage and/or reduced moisture content) of the cucumber fruits and a smaller seed cavity of the fruits compared to the recurrent long cucumber parent. The short, parthenocarpic cucumber line itself (the donor) did not show this phenotype and it was, therefore, a surprise that the long, parthenocarpy cucumber did show this phenotype.

Without wishing to bound, initial mapping studies indicate that one or more QTLs are involved, which confer the increase in dry matter and one or more QTLs are involved which confer the reduction of the seed cavity size. One or more of these QTLs may also have an effect on both seed cavity size and dry matter of the fruits. The short cucumber line is herein referred to as the donor of the small seed cavity (and of the underlying one or more QTLs) and/or of the increase in dry matter (and of the underlying one or more QTLs).

During a breeding program with a short cucumber line, a backcross line was surprisingly found which produced long cucumber fruits with a very small seed cavity and with a dryer fruit flesh appearance and dryer fruit flesh (when pressing fruits cut in half, very little moisture leaked compared to the recurrent parent). In a BC1S1 population, both the small cavity and the dry matter appeared to segregate quantitatively. From this material, a long cucumber inbred line comprising the donor QTLs was been developed which had a very small seed cavity and high dry matter. This line was used as a parent line and was crossed to an elite long cucumber line lacking the donor QTLs, to obtain an F1 hybrid. This F1 hybrid variety is named NUN 09103 CUL.

Plants of cucumber variety NUN 09103 CUL and of a commercial high wire variety called 'Hi Power' (lacking introgressions from the donor, i.e., lacking the QTLs) were grown in the greenhouse in the Netherlands in high-wire cultivation, in order to compare the fruit characteristics. Further, also Consapino RZ was included as a comparison. At various time points (in week 5, 6, 8, 9, 11 and 15 of 2019), representative harvest stage fruits were harvested from 4 different plants per genotype, one fruit from each plant, and the average fruit weight, the average fruit diameter and the average seed cavity diameter of the four fruits was measured. As shown in the Examples and in FIG. 3, fruits of Hi-Power had a large (average) seed cavity diameter, with 48% to 52% of the overall fruit diameter being the seed cavity diameter. On the other hand, in fruits of cucumber variety NUN 09103 CUL the percentage of seed cavity was reduced by at least 3% compared to Hi-Power, with only between 38% to 47% of the overall fruit diameter being seed cavity. The smallest fruit cavity size was found in Consapino RZ, where only 31% to 38% of the overall fruit diameter was seed cavity.

The QTLs present in cucumber variety NUN 09103 CUL (and the parent line) resulted in a reduction in seed cavity diameter by at least 3%, 4%, 5%, 6%, or 7% or more of the normal seed cavity diameter of the control plant lacking the QTLs. However, the reduction in seed cavity diameter was less than in Consapino RZ, and as the donor is a different donor, it appeared that the QTLs in cucumber variety NUN 09103 CUL are different from the QTLs described in WO2016/207432 (and US2018054990) on chromosomes 1 and 2. In WO2016/207432 (and US2018054990), the QTL on chromosome 1 is defined by the SNP haplotype of SEQ ID Nos 3-15 shown in FIG. 3 and the QTL on chromosome 2 is defined by the SNP haplotype of SEQ ID NO:s 18-28 shown in FIG. 3. When doing a BLAST with SEQ ID NO: 3 and 15 against the Cucumber Chinese Long v2 genome (on cucurbitgenomics.org), the QTL region is from nucleotide 9959250 (9.95 Mb) to 18083857 (18.08 Mb) on chromosome 1. When doing a BLAST with SEQ ID NO: 18 and 28 against the Cucumber Chinese Long v2 genome (on cucurbitgenomics.org), the QTL region is from nucleotide 473983 (0.47 Mb) to 3681643 (3.68 Mb) on chromosome 2, i.e., near one end of the chromosome. WO2016/207432 and US2018054990 are incorporated herein by reference.

A representative sample of seeds of cucumber variety NUN 09103 CUL, comprising the QTLs from the donor on the haploid genome (i.e., from the DH parent line), has been deposited under accession number NCIMB 43517, and from the deposit, or from ascendants or descendants of this deposit, the QTLs conferring an increase in dry matter (reduced moisture leakage and/or reduced moisture content) and/or small seed cavity diameter can be easily transferred into any other cucumber type, especially other long cucumber types.

In one embodiment, a cultivated *Cucumis sativus* var. *sativus* plant or plant part is provided comprising one or more introgression fragments from a short cucumber donor plant, wherein said introgression fragments confer in long cucumber an increase in dry matter content of the fruits and/or a reduced seed cavity size compared to a control plant lacking said introgression fragments, wherein said introgression fragments are present in the long cucumber variety NUN 09103 CUL, a representative sample of seeds of said variety have been deposited under accession number NCIMB 43517.

An introgression fragment from the donor comprises a QTL which confers the mentioned increase in dry matter content and/or the mentioned decrease in fruit cavity size when present in long cucumber compared to the control plant (long cucumber lacking the introgression fragments and lacking the QTLs from the donor, such as the genetic control or the recurrent parent).

The QTLs present in cucumber variety NUN 9103 CUL will be mapped using common QTL mapping techniques in order to identify the location of the QTLs and of the introgression fragments in the long cucumber genome. This can, for example, be done by generating a population which segregates for the QTLs of the donor, phenotyping the segregating population for seed cavity size and/or dry matter content, and analyzing the population for e.g., Single Nucleotide Polymorphisms, to generate a marker map of the chromosomes and to map the QTLs in the genome.

Seed cavity size will segregate quantitatively and can be phenotyped e.g., as described in the Examples, by growing plants and measuring the average fruit diameter and seed cavity diameter of fruits.

Dry matter content will also segregate quantitatively and can be phenotyped in different ways e.g., by measuring the moisture leakage from cut pieces of fruits during a defined period of time and under defined conditions (see, e.g., Example 4 of WO2016/207432 and US2018054990, incorporated by reference), or by measuring the amount of moisture released from the cucumber fruits (or parts thereof) when applying a defined pressure to the fruits (or fruit parts) (see e.g., Example 3 of WO2016207432 and US2018054990, incorporated by reference), or other methods, such as weighing fresh cucumbers or cucumber parts, drying them for a certain period of time and then weighing the dried cucumbers or cucumber parts to determine the dry matter percentage by comparing the fresh weight to the dry weight.

The increase in dry matter content of the cucumber fruits, can further be attributed to an increase in dry matter content of the fruit flesh and/or of the fruit cavity (core), by comparing the dry matter content of the fruit flesh, or of the seed cavity, of fruits comprising the one or more QTLs with that of the fruit flesh, or of the fruit cavity, of fruits of the control. In one aspect, the QTLs described herein increase the dry matter content of the fruits by increasing the dry matter content of the fruit flesh. In another aspect, the QTLs described herein increase the dry matter content of the fruits by increasing the dry matter content of the seed cavity. In a further aspect, the QTLs described herein increase the dry matter content of the fruits by increasing the dry matter content of both the fruit flesh and the seed cavity.

In one aspect, the one or more QTLs which confer an increased dry matter content of the fruits (reduced moisture leakage and/or reduced moisture content) and/or the one or more QTLs which confer a smaller seed cavity are introgressed from the donor into a fresh market type cucumber, especially a cucumber type selected from the following types: Beit alpha, Dutch or European Greenhouse type, American slicer or oriental (which can be subdivided into north Chinese, south Chinese and Japanese types), see Guan et al. 2019, HortTechnology 29(5).

In one aspect, the cucumber type is a fresh market type, e.g., a long cucumber type such as a Dutch or European Greenhouse type or a slicer type (e.g., American slicer), producing fruits which have a harvest length (edible maturity or marketable size) of at least about 18 cm, 19 cm, 20 cm, 25 cm, 26 cm, 27cm, 28 cm, 29 cm, 30 cm, 31 cm, 32 cm, 33 cm, 34 cm, 35 cm, 36cm, 37cm, 38 cm or more. In one aspect, the cucumber type is parthenocarpic. In one aspect, the fruit length to fruit diameter ratio is at least 4, 5, 6, 7, 8, 9, 10 or more.

In one embodiment, the plant comprising the one or more QTLs produces fruits wherein (at harvest length/edible maturity/marketable size) the fruit cavity diameter is 38% to 47% of the overall fruit diameter.

In one embodiment, the plant comprising the one or more QTLs produces fruits wherein (at harvest length/edible maturity/marketable size) the fruit cavity diameter is at least 3% smaller than the fruit cavity diameter of the control plant lacking said introgression fragments.

Control plants are plants of preferably the same type and preferably similar genetic background (genetic control or recurrent parent) than the plant comprising the one or more QTLs of the donor, but then the control lacks the QTLs of the donor. For example, when the QTLs are introgressed into a parent elite line, which is referred to as the recurrent parent, that elite line without the QTLs is a suitable control line. However a standard line or variety of the same type may also be used as suitable control.

In one embodiment, the plant comprising the one or more QTLs produces fruits wherein (at harvest length/edible maturity/marketable size) the fruits comprise a dry matter content which is significantly higher than the dry matter content of the fruits produced by a control plant lacking said QTLs (i.e., lacking the introgression fragments from the donor). In one aspect, where the QTLs are introgressed into a long European cucumber type, a suitable control is e.g., the long cucumber variety Hi-Power.

In one embodiment, the plant comprising the one or more QTLs produces fruits wherein (at harvest length/edible maturity/marketable size) the fruits, when cut, have a shelf life which is at least 1 or 2 days longer than the shelf life of fruits produced by a control plant lacking said introgression fragments, such as long cucumber variety Hi-Power. A shelf life test is, for example, described in the Examples, but other tests can be used equally, as long as suitable controls are included. Thus, for example, fruits comprising the one or more QTLs can be sliced and packaged and stored in the same way as fruits of a control plant lacking the QTLs. The dry matter content and/or the small cavity size conferred by the QTLs increases shelf life of the whole fruits, but also especially of the processed fruits. Also processing itself is easier, as less moisture leaks during processing.

In one aspect, the one or more QTLs which confer a reduced seed cavity size and the one or more QTLs which confer an increased dry matter content of the fruits (reduced moisture leakage and/or reduced moisture content) are present in heterozygous form in the plant and in the fruits produced on the plants. The introgression fragment from the donor comprising the QTL may thus be in heterozygous form. In a different aspect, the one or more QTLs are in homozygous form.

In one aspect, the cucumber plant is parthenocarpic and produces seedless fruits without pollination.

In another aspect, the disclosure provides cucumber fruit or a plurality of fruits produced by a plant as described above. In one aspect, the fruits are produced by growing the plants in greenhouses, e.g., with the use of trellises, in an umbrella system or in high-wire cultivation. In one aspect, the fruits are harvested and packaged for fresh consumption or are processed. Fruits are preferably relatively uniform in size and preferably relatively straight for easy packaging or processing.

In another aspect, the fruits or fruit pieces are frozen and optionally thawed. Without wishing to be being bound, it is believed that the increased dry matter content and/or reduced seed cavity size make the fruits and fruit parts suitable for freezing, whereby the thawed fruits or fruit parts are still of good quality and suitable for consumption. Therefore, food or feed products comprising cucumber fruit pieces as described herein can be stored for long periods in frozen form.

In one embodiment, the plant comprising the one or more QTLs is a single cross F1 hybrid or an inbred line.

In a further aspect, the disclosure provides cucumber seeds from which a plant comprising the one or more QTLs can be grown.

In one aspect, the one or more QTLs (or the introgression fragments comprising the QTL) are obtainable by crossing a plant grown from NCIMB 43517 (or ancestors thereof or descendent/progeny therefrom) with another cucumber plant, especially a cultivated cucumber plant, in one aspect a fresh cucumber type, such as a European long cucumber type or an American slicer type. NCIMB 43517 (or ancestors thereof or descendent/progeny therefrom) can thus be used as a source of the one or more QTLs and the one or more QTLs can be introgressed from this source into any other cucumber. The progeny of such a cross can be selected for comprising the one or more QTLs by molecular methods such as marker selection and/or by phenotypic selection of the cavity size and/or the dry matter content of the fruits of the progeny.

As the DH parent line of seeds deposited under NCIMB43517 (NUN 09103CUL F1) comprises the genetic elements that confer the increased dry matter and smaller seed cavity size of the fruits, these genetic elements can be obtained from progeny of cucumber variety NUN 09103CUL F1, either selfing progeny, double haploid progeny or crossing progeny. For example, cucumber variety NUN 09103 CUL can be repeatedly selfed to generate inbred lines having the genetic elements of the parent line (conferring increased dry matter and smaller seed cavity) or double haploid lines can be generated from cucumber variety NUN 09103 CUL F1 and a DH line can be selected having the genetic elements of the parent line (conferring increased dry matter and smaller seed cavity). It is possible to reconstruct the parent lines of an F1 hybrid cucumber as described in WO2014/076249, e.g. on page 10 or page 5. Therefore, in one aspect a cultivated cucumber is provided, especially a long cucumber, comprising the genetic elements of cucumber variety NUN 09103 CUL F1, especially of the DH parent line of cucumber variety NUN 09103 CUL, which result in fruits having the same seed cavity diameter as cucumber variety NUN 09103 CUL, i.e. 38% to 47% of the fruit diameter and/or the same dry matter content as cucumber variety NUN 09103 CUL. Thus, any progeny of cucumber variety NUN 09103 CUL are encompassed herein, be it DH progeny, crossing progeny or selfing progeny, which can be selected to have the genetic elements, as seen by the phenotype of the fruits produced.

In one aspect, a cultivated *Cucumis sativus* var. *sativus* plant is provided comprising one or more introgression fragments on any of the 7 chromosomes in homozygous or heterozygous form, wherein said introgression fragment confers an smaller seed cavity size and/or a higher dry matter content of the fruits produced by the plant compared to the fruits of a cucumber plant lacking the introgression fragments, e.g., the genetic control or control variety, when grown under the same conditions.

The average seed cavity (also referred to as fruit cavity) diameter of the fruits is preferably expressed as a percentage of the average fruit diameter of the fruits. In one aspect, the one or more QTLs reduce the percentage by at least 3%, 4%, 5%, 6%, 7% or more. FIG. 3 shows, for example, that the fruit cavity diameter of cucumber variety NUN 09103 CUL is reduced by at least 3% compared to the control, Hi-Power. In cucumber variety NUN 09103 CUL, the fruit cavity diameter is 38% to 47% of the overall fruit diameter, while in the control it is 48% to 52% of the overall fruit diameter, i.e., in cucumber variety NUN 09103 CUL there is a reduction of 3% to 13%.

This fruit cavity diameter and fruit diameter are preferably measured somewhere in the middle of the fruits and not near the ends of the fruits. The measurements should be done for a number of representative, harvest stage fruits from a number of plants grown under the same conditions.

Likewise, the measurements for dry matter content of the fruits are preferably done for a number of representative, harvest stage fruits from a number of plants grown under the same conditions.

As mentioned, different types of experiments can be done to determine the average dry matter content, e.g., measuring moisture leakage of cut fruit pieces or applying pressure to cut fruit pieces or comparing fresh weight and dry weight of fruits or fruit pieces. The presence of the one or more QTLs from the donor increase the dry matter content in a statistically significant way compared to the control lacking the QTLs.

Mapping of the QTLs for seed cavity size and for dry matter content, which can be found in the deposited seeds, will identify the chromosomes of the plant and the chromosome regions comprising introgression fragment from the donor on which the QTLs are found, as well as SNP markers to identify the donor fragments comprising the QTLs. Several QTLs may be on a single chromosome, i.e., a chromosome may comprise a single introgression fragment with one or more QTLs or a chromosome may comprise 1, 2 or more introgression fragments, each having e.g., one QTL. As mentioned, a QTL may either affect only seed cavity size, it may affect only dry matter content, or it may affect both cavity size and dry matter content. QTLs may also interact, i.e., the effect may be epistatic. A QTL may be dominant, recessive or have intermediate or incomplete dominance. In cucumber variety NUN 09103 CUL, only one parent line comprises the introgression fragments from the donor, indicating that the QTLs are likely dominant. A recombinant chromosome refers herein to a chromosome which comprises at least one fragment of the donor chromosome which fragment comprises at least one QTL for small cavity size and/or increased dry matter content. As cucumber is diploid, the plant can comprise one or two recombinant chromosomes, i.e., it is heterozygous or homozygous for the recombinant chromosome.

In one aspect, the plants described herein comprise a genome of a cultivated cucumber, e.g., a long cucumber type, with at least one or two recombinant chromosomes (i.e., heterozygous or homozygous) and said recombinant chromosome comprising at least one QTL for small cavity size and/or increased dry matter content. The recombinant chromosomes thus comprise a fragment of the short cucumber donor, which is distinguishable from recipient cucumber genome by e.g., molecular marker analysis or whole genome sequencing and/or by growing the plants together with control plants and comparing the phenotypes of the fruits to e.g., those of cucumber variety NUN 09103 CUL, deposited herein under NCIMB 43517. Other suitable comparisons are variety Hi-Power, and also Consapino RZ can be included as comparison.

In one aspect, the presence of the introgression fragment in the genome of the plant or plant cell or plant tissue (or in the DNA extracted therefrom) is detectable by a molecular marker assay which detects one or more molecular markers of the introgression fragment, i.e., markers, such as SNP markers, which distinguish the introgression fragment comprising the QTL from fragments lacking the QTL. However, other techniques may be used, e.g., whole genome sequencing.

When reference is made herein to one or more molecular markers being "detectable" by a molecular marker assay, this means that the plant or plant part comprises the one or more markers in its genome, as the marker would otherwise not be detectable.

Thus, the introgression fragment (and a cultivated cucumber plant or plant part, e.g., a cell, comprising the introgression fragment) can be detected in a marker assay by detecting the SNP genotype or haplotype of the introgression fragment (i.e., of the donor cucumber germplasm) of one or more or all of the markers.

The QTL, or the introgression fragment comprising the QTL, is in one aspect dominant, i.e., it is sufficient to have the introgression fragment on one of the chromosomes (one recombinant chromosome), while the homologous chromosome of the pair may be a (non-recombinant) chromosome of cultivated C. sativus var. sativus lacking the introgression fragment.

In a specific embodiment, the one or more introgression fragment comprising the one or more QTLs for small seed cavity and/or increased dry matter content is derivable from (or derived from) or obtainable from (or obtained from; or as present in) seeds, a representative sample of which has been deposited under accession number NCIMB 43517, or from progeny thereof. The progeny may be any progeny which retain the one or more (or all) SNP markers indicative of (and linked to) the QTLs and/or progeny which retain the phenotype for smaller seed cavity diameter and/or higher dry matter content compared to a control as e.g., seen in fruits of NCIMB 43517. Thus, progeny are not limited to F1 or F2 progeny of the deposit, but can be any progeny, whether obtained by selfing and/or crossing, such as backcrossing, with another cucumber plant.

Thus, in one aspect, the disclosure relates to a cultivated Cucumis sativus var. sativus plant comprising at least one introgression fragment from a short cucumber donor, wherein said introgression fragment is an introgression fragment "as in"/"identical to"/"the same as in" the seeds deposited under number NCIMB 43517.

The cultivated cucumber plant described herein may be an inbred line, an OP (open pollinated variety) or an F1 hybrid. An F1 hybrid is produced by crossing two inbred parent lines, one of which possesses the introgression fragment(s) (preferably in homozygous form, although not necessarily) and collecting the F1 hybrid seeds from said cross. In another aspect, the F1 hybrid may comprise the introgression fragment(s) in homozygous form, i.e., produced by crossing two inbred parent lines, each comprising the introgression fragment(s) in homozygous or heterozygous form.

The cultivated cucumber plant may be of any type, but in one aspect it is preferably not a short cucumber type. Short cucumber types produce fruits of about 14 to 16 cm, without a neck, with a smooth or slightly ribbed skin and with parthenocarpy fruit formation. They are awarded a score of 3 for the length of the fruit according to the CPVO Protocol for tests on distinctness, uniformity and stability (CPVO/TP-061/2 Rev 2, see characteristic 17 in the Table of Characteristics; see also world wide web at cpvo.europa.eu/ en/applications-and-examinations/technical-examinations/technical-protocols/cpvo-technical-protocols).

Preferably, the cucumber plant is a fresh market type, e.g., a Beit alpha, a long cucumber type, a European or Dutch Greenhouse cucumber type, an American slicer type or an oriental type. Preferably it has good agronomic and good fruit quality characteristics. The cultivated cucumber plant is in one aspect uniform, both genetically and phenotypically. Especially fruit characteristics are uniform, e.g., regarding shape, skin color, skin thickness, skin ribs, skin toughness, spines (spine color, spine density, etc.), presence/absence of warts, length and diameter at edible and marketable maturity, flavor, etc. Likewise seed characteristics (i.e., characteristics of the seeds from which the plant is grown) are uniform, e.g., seed size, seed color, etc. Thus, plants of the line or variety comprising one or more of the QTLs in homozygous or heterozygous form produce uniform fruits, meaning that there is little variation between fruits of plants grown under the same environmental conditions and when fruits are at the same developmental stage (e.g., for qualitative characteristics at least 98%, 99% or preferably 100% of all plants or plant parts, fruits or seed are identical for the characteristics; for quantitative characteristics at least 90%, 95%, 98% of all plants or plant parts, fruits or seed are identical for the characteristics).

The cultivated cucumber plant comprising one or more QTLs described herein may be of one of the following cucumber types: slicing cucumbers (e.g., American slicing), long cucumbers, European greenhouse cucumbers, Beit-Alpha type cucumbers, oriental trellis type cucumbers, Asian cucumbers (e.g., selected from Indian Mottled cucumber, Chinese Long cucumber, Korean cucumber and Japanese cucumber type).

In one aspect, the cultivated cucumber is an inbred line or a F1 hybrid of a slicing cucumber type, long cucumber type, European greenhouse cucumbers, Beit-Alpha type cucumbers, oriental trellis type cucumbers, Chinese long cucumber type, Korean cucumber type or Japanese cucumber type. In a specific embodiment the cucumber is an inbred line or an F1 hybrid of a long cucumber, especially a European greenhouse cucumber.

In one aspect, the F1 hybrid is a long cucumber type, e.g., a European greenhouse cucumber type, suitable for the traditional glasshouse cultivation or for high-wire cultivation. In the traditional glasshouse cultivation method the main stem of the plant is led up to a horizontal iron wire that is suspended at a height of about two meters above the ground. When the plant reaches this height and attaches to the wire, it is "topped" by removing its growth point in order to terminate further proliferation, whereupon lateral shoots start to develop. These lateral shoots are allowed to grow downward to a height of about 1 meter above the ground, and the growth points are then removed from them. This is followed by flowering and the development of the fruits both on the stem and on the lateral shoots or tendrils, but the fruits on the tendrils develop later than those on the stem.

In the high-wire cultivation no lateral tendrils are allowed to grow and all the harvest comes from the stem. Specific varieties have been developed by Nunhems which are highly suitable for high-wire cultivation, as they provide a gene called "compact", see, WO2009/059777 and U.S. Pat. No. 8,710,303, for example varieties Hi Jack, Hi Power, Hi Lisa. Thus, in one aspect, the cultivated cucumber plant comprises additionally the compact gene described in WO2009/059777 and U.S. Pat. No. 8,710,303, which are incorporated by reference herein.

In another aspect, the one or more introgression fragments described herein are present in a long cucumber type. A "long cucumber type" or "long cucumber plants" are greenhouse cucumbers characterized by fruits of at least about 26 cm or 27 cm to 37 or 38 cm in length, or longer (for example 40 cm, 42 cm or more), preferably with parthenocarpic fruit formation. Examples of long cucumber types are the Sabrina and Korinda or the varieties Hi Jack, Hi Power, Hi Lisa or cucumber plants that are awarded a score of 7-9 for the length of the fruit according to the CPVO Protocol for tests on distinctness, uniformity and stability (CPVO/TP-061/2 Rev 2, see, characteristic 17 in the Table of Characteristics; see, also world wide web at cpvo.europa.eu/en/applications-and-examinations/technical-exami nations/technical-protocols/cpvo-technical-protocols). Other long cucumber varieties are, for example, Bodega, Bologna, Corona, Kamaro, Flamingo, Discover, Kalunga, Kasja, Logica, Millagon, Nicola, Milika, Manuela, Frida, Activa, Alaya, Savanna, Sienna, Bella, Sheila, and Bornand.

In another aspect, the one or more introgression fragments described herein are present in a American Slicer cucumber type. A "American slicer type" are greenhouse cucumbers characterized by fruits of at least about 18 cm or 19 cm to 23 or 24 cm in length, or longer (for example 30 cm, 32 cm or more), preferably with parthenocarpic fruit formation. Examples of American slicer cucumber types are the Jazzer, Sprint and Marketmore varieties, or cucumber plants that are awarded a score of 5-7 for the length of the fruit according to the CPVO Protocol for tests on distinctness, uniformity and stability (CPVO/TP-061/2 Rev 2, see, characteristic 17 in the Table of Characteristics). Other American Slicer varieties are Corinto, Lisboa, Alcazar, and Sweet Success.

In one aspect, the European greenhouse cucumber is the plant of which seeds were deposited under accession number NCIMB 43517, or progeny thereof, whereby the progeny retains one or more of the introgression fragments comprising a QTL from the donor (as detectable by the presence of one or more markers of the introgression fragment and/or the phenotype conferred by the QTL).

In another aspect, the plant is not a wild cucumber plant or a wild relative of cucumber or a landrace.

In yet another aspect, the plant is a cultivated cucumber of the Eurasian cucumber group, the East Asian cucumber group or the Xishuangbanna cucumber group. In another aspect, the plant is not a cucumber of the Indian cucumber group.

In one embodiment, the cultivated cucumber plant comprising one or more of the QTLs for small seed cavity and/or for increased dry matter content produces seedless fruits without pollination, i.e., is parthenocarpic. Such seedless fruits are also encompassed herein. In another aspect, the cultivated cucumber plant comprising one or more of the QTLs for small seed cavity and/or for increased dry matter are not parthenocarpic.

In a further embodiment, the cultivated cucumber plant comprising one or more of the QTLs for small seed cavity and/or for increased dry matter content is primarily gynoecious or entirely gynoecious. In a further embodiment, the cultivated cucumber plant comprising one or more of the QTLs for small seed cavity and/or for increased dry matter content is monoecious or hermaphroditic.

In a further embodiment, the cultivated cucumber plant comprising one or more of the QTLs for small seed cavity and/or for increased dry matter content is uniform and genetically stable regarding the morphological characteristics of the fruits produced by said plant, e.g., regarding fruit shape, fruit color, skin thickness, warts, etc.

Fruit characteristics, such as average fruit length, average fruit diameter, skin thickness, presence/absence of warts, spininess, skin toughness, skin color, fruit neck shape, fruit tapering, shape of medial cross section, presence or absence of seeds (parthenocarpy), etc. depend on the cucumber type, i.e., the cultivated genetic background (gene pool) into which the QTL(s) is (are) introgressed. Thus, depending on the cucumber type, various fruit shapes, sizes and fruit types are included herein. In one aspect, the fruits are seedless. In another aspect, the fruits are seeded.

The two main types of cucumber fruit grown commercially today in the United States are fresh market (slicing) type and the processing (pickling) type. Varieties and production methods are typically adapted to the end use. Slicing cucumbers are often longer, larger and have darker and thicker skin, whereas pickling/processing cucumbers have a shorter fruit, thinner skin with interior flesh that make them more amenable to pickling. Seedless varieties are generally preferable for both fresh market and for pickling as developing and large seeds are not palatable.

In one aspect, the plant is a fresh market type, e.g., a long cucumber type or slicing type, and produces fruits have an average fruit length at edible maturity and/or marketable size which is e.g., at least 18 cm, 19 cm, 20 cm, 25 cm, 26 cm, 27 cm, 28 cm, 29 cm, 30 cm, 32 cm, 40 cm, or more. In one aspect, the fruit length/diameter ratio is at least 4, preferably at least 5, 6, 7, 8, 9, 10 or more.

In one aspect, the cucumber plant is a long cucumber type and has an average fruit length at edible maturity and/or marketable size of at least 30 cm, preferably at least 31 cm or at least 32, 33, 34, 35, 36, 37 or 38 cm.

In a preferred aspect, the plant is a long cucumber type producing fruits of marketable size, especially seedless fruits. The fruits of marketable size, and parts thereof, and food or feed products containing these, are also encompassed herein. In one embodiment the SNP markers are detectable in the fruits, fruit parts or food or feed products comprising these.

In one aspect, the fruits have, at harvest maturity, an average fruit weight of at least 390 g, 395 g, 400 g, 405 g, 410 g, 420 g, 430 g, 440 g, 450 g, or more.

In one aspect, the plant is an indeterminate cucumber. In another aspect, the cucumber is determinate.

Also seeds from which a plant described herein can be grown is provided herein, as are cucumber fruits harvested from a plant described herein. These comprise the QTL(s) in their genome and can therefore be distinguished from other fruits by the presence of one or more of the SNP markers linked to the QTL(s).

In one aspect, the fruits are bitter free (selected from the groups bitter and bitter free) at edible maturity and/or at marketable size of the fruits.

In a further aspect, the fruit has a thin skin (selected from the groups thick and thin) at edible maturity and/or at marketable size of the fruits.

The terms edible maturity, marketable size and harvest maturity (or harvest length) are used interchangeably herein and refer to the stage at which cucumber fruits are harvested in their cultivation, for fresh sale or for processing.

In another embodiment, the QTL(s) is (are) introgressed into a cucumber type called 'Compact', as described in U.S. Pat. No. 8,710,303 (and incorporated by reference herein). Thus, the cucumber plants described herein comprise the compact gene as described in U.S. Pat. No. 8,710,303 in homozygous or heterozygous form, e.g., as present in varieties Hi Jack, Hi Power, Hi Lisa and others (Nunhems varieties).

In a further embodiment, the disclosure provides a plant cell, tissue or plant part of a plant or of a seed described herein.

Also the use of a recombinant chromosome comprising an introgression fragment from a short cucumber donor (said introgression fragment comprising an allele conferring a smaller seed cavity diameter and/or an increased dry matter content) for breeding cucumber varieties having a smaller seed cavity diameter and/or an increased dry matter content is encompassed herein. In one aspect, said recombinant chromosome is a recombinant chromosome as found in seeds deposited under accession number NCIMB 43517, or is derived from said recombinant chromosome (e.g., comprises a smaller fragment of the introgression fragment found in said seeds).

Likewise, the use of one or more recombinant chromosomes as found in seeds deposited under accession number NCIMB 43517, or in progeny thereof, for generating a cultivated cucumber plant comprising an smaller seed cavity diameter and/or an increased dry matter content of the fruits compared to a control plant lacking the recombinant chromosomes is encompassed herein, wherein said recombinant chromosomes confer a smaller seed cavity diameter and/or an increased dry matter content of the fruits compared to the control cucumber plant lacking said introgression fragments, such as the genetic control or a control breeding line or variety.

Also the use of a one or more introgression fragments from a short cucumber donor (said introgression fragment comprising one or more QTLs conferring a smaller seed cavity diameter and/or an increased dry matter content) for breeding cucumber varieties having a smaller seed cavity diameter and/or an increased dry matter content is encompassed herein. In one aspect, said introgression fragments are the introgression fragments as found in seeds deposited under accession number NCIMB 43517, or is derived from said introgression fragments (e.g., comprises a smaller fragment of the introgression fragment found in said seeds).

Likewise, the use of one or more introgression fragments as found in seeds deposited under accession number NCIMB 43517, or in progeny thereof, for generating a cultivated cucumber plant comprising an smaller seed cavity diameter and/or an increased dry matter content of the fruits compared to a control plant lacking the introgression fragments is encompassed herein, wherein said introgression fragments confer a smaller seed cavity diameter and/or an increased dry matter content of the fruits compared to the control cucumber plant lacking said introgression fragments, such as the genetic control or a control breeding line or variety.

Similarly, the use of plants grown from seeds deposited under accession number NCIMB 43517 or progeny thereof, for generating a cultivated cucumber plant comprising a smaller seed cavity diameter and/or an increased dry matter content of the fruits is encompassed herein, wherein said smaller seed cavity diameter and/or an increased dry matter content of the fruits is conferred by an introgression fragment obtained from one or more of the 7 chromosomes of said plants or progeny thereof.

In one aspect variety, cucumber variety NUN 09103 CUL is provided, a representative sample of seeds has been deposited under accession number NCIMB 43517, which variety produces fruits having an average seed cavity diameter of 38% to 47% of the average fruit diameter.

In one aspect, progeny of cucumber variety NUN 09103 CUL are provided, wherein the progeny produces fruits having an average seed cavity diameter of 38% to 47% of the average fruit diameter.

In one aspect, variety NUN 09103 CUL is provided, a representative sample of seeds has been deposited under accession number NCIMB 43517, which variety produces fruits wherein the fruit cavity diameter is at least 3% smaller than the fruit cavity diameter of cucumber variety Hi Power.

In one aspect, progeny of cucumber variety NUN 09103 CUL are provided, wherein the progeny produces fruits wherein the fruit cavity diameter is at least 3% smaller than the fruit cavity diameter of cucumber variety Hi Power.

In one aspect, variety NUN 09103 CUL is provided, a representative sample of seeds has been deposited under accession number NCIMB 43517, which variety produces fruits having a dry matter content significantly higher than the dry matter content of fruits produced by cucumber variety Hi Power.

In one aspect, progeny of cucumber variety NUN 09103 CUL are provided, wherein the progeny produces fruits having a dry matter content significantly higher than the dry matter content of fruits produced by cucumber variety Hi Power.

In one aspect, variety NUN 09103 CUL is provided, a representative sample of seeds has been deposited under accession number NCIMB 43517, which variety produces fruits that when cut have a shelf life at least 2 days longer than the shelf life of fruits produced by cucumber variety Hi Power.

In one aspect, progeny of cucumber variety NUN 09103 CUL are provided, wherein the progeny produces fruits that when cut have a shelf life at least 2 days longer than the shelf life of fruits produced by cucumber variety Hi Power.

In one aspect, variety NUN 09103 CUL is provided, a representative sample of seeds has been deposited under accession number NCIMB 43517, which variety has a combination of the following characteristics: fruits produced have an average seed cavity diameter of 38% to 47% of the average fruit diameter, the average fruit cavity diameter is reduced by at least 3% compared to the control variety Hi Power, the fruits, when cut, have a shelf life which is at least 1 or 2 days longer than the shelf life of fruits produced by cucumber variety Hi Power.

In one aspect, progeny of variety NUN 09103 CUL are provided, a representative sample of seeds has been deposited under accession number NCIMB 43517, which progeny has a combination of the following characteristics: fruits produced have an average seed cavity diameter of 38% to 47% of the average fruit diameter, the average fruit cavity diameter is reduced by at least 3% compared to the control variety Hi Power, the fruits, when cut, have a shelf life which is at least 1 or 2 days longer than the shelf life of fruits produced by cucumber variety Hi Power.

In one aspect, the progeny are produced by crossing cucumber variety NUN 09103 CUL with another long cucumber line or by selfing cucumber variety NUN 09103 CUL one or more times or by producing double haploid lines from cucumber variety NUN 09103 CUL and selecting a progeny having a combination of the following characteristics: fruits produced have an average seed cavity diameter of 38% to 47% of the average fruit diameter, the average fruit cavity diameter is reduced by at least 3% compared to the control variety Hi Power, the fruits, when cut, have a shelf life which is at least 1 or 2 days longer than the shelf life of fruits produced by long cucumber variety Hi Power.

Furthermore, a method of producing *C. sativus* plants comprising one or more introgression fragments conferring a smaller seed cavity diameter and/or an increased dry matter content of the fruits is provided comprising:

a) providing a first inbred cucumber plant comprising one or more recombinant chromosomes in homozygous form having one or more introgression fragments comprising one or more QTLs conferring a smaller seed cavity diameter and/or an increased dry matter content of the fruits, optionally wherein said introgression fragments or said recombinant chromosomes are as present in and/or derived from NCIMB 43517, or from progeny thereof retaining the introgression fragment and the capability to produce fruits having a small fruit cavity and/or an increased dry matter content;
b) providing a second inbred cucumber plant;
c) crossing said cucumber plant of a) with said cucumber plant of b); and
d) collecting F1 hybrid seeds from said cross.

The F1 hybrid seeds collected are also provided herein.

In another aspect, a method for generating progeny of NCIMB 43517 is provided, said method comprising:

a) growing a plant from seeds deposited under accession number NCIMB 43517;
b) selfing said plant one or more times and/or crossing said plant one or more times with another cucumber plant to generate progeny seeds, or producing double haploid lines from plants grown from seeds deposited under accession number NCIMB 43517; and
c) identifying and/or selecting a progeny plant comprising one or more QTLs conferring a smaller seed cavity diameter and/or an increased dry matter content of the fruits compared to a control, such as Hi Power.

The cucumber plant in step b) is preferably a cultivated cucumber, such as a European greenhouse cucumber or long cucumber type.

In step c), phenotypic selection may be used and/or marker assisted selection may be used, using markers linked to one or more of the QTLs which confer small seed cavity diameter and/or high dry matter content present in NCIMB 43517.

A progeny plant generated by the above method is also provided herein. The progeny plant may comprise one or more or all of the recombinant chromosomes present in NCIMB 43517 or one or more or all of the introgression fragments present in NCIMB 43517.

In a further aspect, also a variety named NUN 09103 CUL is provided, a representative sample of seeds having been deposited under accession number NCIMB 43517.

In a further aspect, also a progeny plant of variety NUN 09103 CUL is provided, a representative sample of seeds having been deposited under accession number NCIMB 43517, said progeny plant retaining the combination of fruit phenotypes of cucumber variety NUN 09103 CUL, especially the fruits produced by the progeny have an average seed cavity diameter of 38% to 47% of the average fruit diameter, and/or the average fruit cavity diameter of the fruits is reduced by at least 3% compared to the variety Hi Power, and/or the fruits, when cut, have a shelf life which is at least 1 or 2 days longer than the shelf life of fruits produced by long cucumber variety Hi Power.

Also a method of making a progeny plant of variety NUN 09103 CUL is provided, comprising:

a) crossing cucumber variety NUN 09103 CUL one or more times with another cucumber line and/or selfing cucumber variety NUN 09103 CUL one or more times and/or generating double haploid lines from cucumber variety NUN 09103 CUL to produce progeny of cucumber variety NUN 09103 CUL; and
b) selecting a progeny plant or line from the progeny produced in step a) which retains the combination of fruit phenotypes of cucumber variety NUN 09103 CUL, especially the fruits produced by the progeny line have an average seed cavity diameter of 38% to 47% of the average fruit diameter, and/or the average fruit cavity diameter of the fruits is reduced by at least 3% compared to the variety Hi Power, and/or the fruits, when cut, have a shelf life which is at least 1 or 2 days longer than the shelf life of fruits produced by long cucumber variety Hi Power.

Such a progeny plant or line can thus be an F1, F2, F3, F4, etc. or a S1, S2, S3, S4, etc., or a BC1, BC2, BC3, BC4 etc. or a DH line.

Optionally the progeny plant or line may contain one or more other characteristics of cucumber variety NUN 09103 CUL, when grown under the same environmental conditions.

The other cucumber line in step a is preferably a long cucumber type.

A progeny line may be used as a parent line to make F1 hybrid seeds and plants grown from said seeds, which produce fruits that have an average seed cavity diameter of 38% to 47% of the average fruit diameter, and/or the average fruit cavity diameter of the fruits is reduced by at least 3% compared to the variety Hi Power, and/or the fruits, when cut, have a shelf life which is at least 1 or 2 days longer than the shelf life of fruits produced by long cucumber variety Hi Power.

Thus a progeny of cucumber variety NUN 09103 CUL may be an F1 hybrid, an inbred line, a double haploid line, optionally an F1 hybrid having a DH progeny line as parent, wherein the DH progeny line produces fruits that have an average seed cavity diameter of 38% to 47% of the average fruit diameter, and/or the average fruit cavity diameter of the fruits is reduced by at least 3% compared to the variety Hi Power, and/or the fruits, when cut, have a shelf life which is at least 1 or 2 days longer than the shelf life of fruits produced by long cucumber variety Hi Power.

Also containers and packages containing or comprising seeds from which plants described herein can be grown are provided herein. These may be labelled as containing cultivated cucumber seeds producing fruits having a small seed cavity and/or high dry matter content. In one aspect the seeds of plants may be referred to as "intense cucumber".

Also progeny seeds and progeny plants of plants described herein are provided, which retain the one or more introgression fragments from the donor, or which comprise one or more smaller introgressions (e.g., subfragments derivable from the introgression fragments as present in NCIMB 43517), which still comprise the QTL for small seed cavity and/or high dry matter content. Progeny may be any generation obtained by selfing a cucumber plant described herein and/or crossing a cucumber plant described herein with another cucumber plant one or more times. Progeny are, therefore, either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g., the F2) with another cucumber plant. Progeny are preferably selected to retain the introgression fragments from the donor cucumber (comprising the QTL(s)). Thus progeny also have a smaller seed cavity diameter and/or the higher dry matter content phenotype compared to a suitable control, optionally the same or similar seed cavity diameter and/or the same or similar dry matter content as the plant used in the initial cross or selfing, e.g., as NCIMB 43517. However, if not all QTLs are retained in the progeny, then the effect on the seed cavity diameter and/or on the dry matter content may be not as strong as in NCIMB 43517. The presence of (or retention of) the introgression fragments comprising the QTLs can be determined phenotypically and/or using the molecular marker assay(s) of markers linked to the QTLs.

In a further aspect, parts of the cucumber plants described herein are provided. Parts include for example cells and cell-cultures, tissue cultures, vegetative plant tissues (leaves, roots, etc.), flowers, pollen, embryos, fruits, parts of fruits, etc. The plant parts comprise one or more of the introgression fragments, as described, and can be detected using one or more of the markers linked to the QTLs. Also, when whole plants are regenerated from such cucumber parts, such as cells, cell- or tissue cultures, the regenerated plants comprise the one or more introgression fragments with the QTLs and the phenotype conferred by the QTLs.

Thus, also provided is a plant cell, tissue or plant part of a plant or of a seed of the plants described herein.

Also in vitro cell cultures and in vitro tissue cultures are encompassed herein, of cells or tissues from plants described herein. Preferably, the cells or tissues can be regenerated into a whole cucumber plant, i.e., the cells are regenerable cells and the tissues comprise regenerable cells. Thus, also vegetative propagations of the plants described herein are provided. Thus, a vegetatively propagated cultivated cucumber plant is provided in one aspect. In a different aspect, non-propagating cells comprising one or more of the QTLs are encompassed herein, as are tissues comprising such cells.

In a specific aspect, a cucumber fruit harvested from a plant described herein is provided. Marketable size cucumber fruits, especially for the fresh market (slicing), are generally graded according to fruit size and quality characteristics after harvest. See e.g., the United States Standards for Grades of Cucumbers, US Department of Agriculture, see the world wide web at ams.usda.gov/grades-standards/cucumber-grades-and-standards. Herein different grades of cucumbers are distinguished. Thus, in one aspect harvested fruits are provided of U.S. Fancy grade, U.S. Extra No. 1 grade, U.S. No. 1 grade, U.S. No. 1 Small grade, U.S. No. 1 Large grade, U.S. No. 2 grade. Also containers or packages comprising or consisting of harvested cucumber fruits are provided.

In another aspect, the cucumber is a long cucumber type or an American slicer and fruits harvested and optionally processed (e.g., sliced or diced) are provided. In one aspect, the fruit cavity is removed from the fruits, as fruit pieces without the fruit cavity have an even longer shelf life than fruit pieces with cavity, see Examples.

The disclosure also provides for a food or feed product comprising or consisting of a plant part described herein preferably a cucumber fruit or part thereof and/or an extract from a plant part described herein. The food or feed product may be fresh or processed, e.g., pickled, canned, steamed, boiled, fried, blanched and/or frozen, etc. For example, containers such as cans, boxes, crates, bags, cartons, Modified Atmosphere Packaging, films (e.g., biodegradable films), etc. comprising plant parts such as fruits or fruit parts (fresh and/or processed) described herein are also provided herein.

In a further embodiment, the disclosure provides for a method of producing a new cultivated cucumber plant which comprises one or more introgression fragments (which confer a smaller seed cavity diameter and-or a higher dry matter content) in homozygous or heterozygous form. The method comprises crossing a plant described herein, or a progeny plant thereof, either as male or as female parent, with a second cucumber plant one or more times, and/or selfing a cucumber plant described herein, or a progeny plant thereof, one or more times, and selecting progeny from said crossing and/or selfing.

Thus, a method for transferring one or more of the introgression fragments (or one or more of the recombinant chromosomes comprising these) from one (cultivated) cucumber plant into another (cultivated) cucumber plant is provided, especially into cucumber varieties or breeding lines for which the seed cavity diameter should be decreased or for which the dry matter content should be increased, or both.

The method comprises the steps of:
a) providing a first cultivated cucumber plant comprising one or more introgression fragments said introgression fragments comprising one or more QTLs which confer a smaller fruit cavity size or a higher dry matter content, or both, compared to a control lacking all of said introgression fragments;
b) providing a second cultivated cucumber plant, especially a plant lacking said introgression fragments;
c) crossing said cucumber plant of a) with said cucumber plant of b);
d) collecting F1 hybrid seeds from said cross; and
e) optionally selfing the plant grown from said F1 hybrid seeds to produce F2 seeds or further selfing generations, and optionally selecting the F2 seeds or further selfing generation seeds; and/or
f) optionally breeding further with plants grown from said F1 or F2 or further generation selfing seeds to produce a cucumber plant having good agronomic characteristics and comprising one or more of the introgression fragments in homozygous or heterozygous form.

The presence or absence of the recombinant chromosomes or of the introgression fragments, may be determined by one or more of the molecular marker assays of markers linked to the QTLs and/or by determining whether the dry matter content is significantly increased compared to the plant of step b) and/or whether the seed cavity diameter is significantly reduced compared to the plant of step b).

The introgression fragments in the plant of step a) are in one aspect one or more of the fragments present in NCIMB 43517. Also, the one or more introgression fragments in step f) are in one aspect one or more of the fragments present in NCIMB43517. Thus, in step a) a plant of NCIMB 43517 or an ancestor (especially the parent line comprising the donor QTLs) or progeny thereof may be used, which comprises one or more of the QTLs present in NCIMB 43517.

The parents of a hybrid can be reconstructed from the hybrid, using methods for reconstructing an F1 hybrid using the method described in WO2014/076249 (or US2015245570), where are incorporated by reference herein. Basically, an F1 hybrid variety is selfed and selfing progeny, or alternatively the double haploids produced, are screened using a large set of molecular markers (distributed across the entire cucumber genome) which are heterozygous in the original F1 hybrid, in order to select two progeny plant lines which are fixed for complementary chromosome regions, which chromosome regions then reconstitute the F1 hybrid genome when the two lines are crossed with each other. The development of large sets of molecular markers and their use in screening and selection of plants is routine in cucumber.

Further breeding in step f) may comprise selfing, crossing, double haploid production, backcrossing, and combinations thereof (e.g., backcrossing and selfing), etc. Plants, plant parts and seeds obtainable by the above method are encompassed herein.

Also provided is a method of producing cultivated cucumber F1 hybrid plants comprising one or more QTLs which confer a small seed cavity and/or a high dry matter content, comprising:
a) providing a first inbred cucumber plant comprising at least one recombinant chromosome comprising an introgression fragment comprising a seed cavity size QTL and/or a dry matter QTL,
b) providing a second inbred cucumber plant lacking the QTLs of a),
c) crossing said cucumber plant of a) with said cucumber plant of b),
d) collecting F1 hybrid seeds from said cross.

The inbred cucumber plant of a) and b) may be homozygous and/or heterozygous for the introgression fragment comprising the QTL. In one aspect, the introgression fragment or fragments in the plant of step a) are in one aspect one or more of the introgression fragments present in NCIMB 43517, especially present in the parent line of NCIMB 43517 (comprising the QTLs from the donor). Thus, in step a) an inbred cucumber plant derived from NCIMB 43517, or an ancestor of NCIMB 43517 (especially the parent line comprising the donor QTLs), which comprises one or more of the QTLs present in NCIMB 43517 may be used.

In one embodiment, plants derived from cucumber variety NCIMB 43517, e.g., progeny thereof, e.g., obtained by selfing and/or crossing and/or double haploid production and retaining one or more of the introgression fragments (and one or more of the QTLs) are used as a parent line for F1 hybrid seed production.

The F1 hybrid seeds preferably comprise at least one of the introgression fragments of NCIMB 43517 conferring smaller seed cavity size and/or increased dry matter content of the fruits and the F1 plants grown from the seeds do therefore produce fruits having a smaller seed cavity size and/or an increased dry matter content compared to the control lacking the introgression fragments, such as e.g., Hi Power.

Plants and seeds obtainable by the above method are encompassed herein.

In a different aspect, a method for producing a cultivated cucumber plant comprising one or more introgression fragments which confer a smaller seed cavity size and/or increased dry matter content of the fruits, is provided, said method comprising the steps:
a) providing a first cultivated cucumber plant;
b) providing a second donor cucumber plant, wherein said donor plant comprises one or more QTLs that confer a smaller seed cavity size and/or increased dry matter content of the fruits, as determinable by the presence of one or more SNP markers linked to the QTLs and/or by the phenotype of the fruits;
c) crossing said cucumber plant of a) with said cucumber plant of b);
d) collecting F1 seeds from said cross and backcrossing an F1 plant to the cucumber plant of a) to produce a backcross (BC1) population, or selfing said F1 plants one or more times to produce an F2 or F3 or higher generation selfing population;
e) optionally backcrossing a plant of d) one or more times to the cucumber plant of a) to produce a higher generation backcross population; and f) identifying a F2, F3, or higher generation selfing, or BC1 or higher generation backcross plant which comprises one or more of the QTLs of the donor cucumber plant.

When referring to backcross populations in the method, the backcross populations may also be selfed, i.e., BC1S1, BC1S2, BC2S1, BC2S2, or others.

In one or more of steps b) to f), the presence of the one or more QTLs (or the introgression fragment comprising the QTL) may be tested (and plants may be selected) by carrying out a molecular marker assay of the markers linked to the QTLs, and/or by analyzing the fruit phenotype (seed cavity diameter and/or dry matter content).

The donor in step b) is in one aspect NCIMB 43517 or an ancestor or progeny of NCIMB 43517, as described, comprising one or more or all of the introgression fragments present in NCIMB 43517.

Using this method, one can generate and/or select new cultivated cucumber plants comprising one or more introgression fragments from a donor source.

A method for generating progeny of NCIMB 43517 is provided, said method comprising:
- a) growing a plant from seeds deposited under accession number NCIMB 43517;
- b) selfing said plant one or more times or crossing said plant one or more times with another cucumber plant to generate progeny seeds or generating double haploids from NCIMB 43517 or from said progeny seeds to generate DH progeny;
- c) screening said progeny seeds or DH progeny or plants grown from said seeds or parts of the seeds or plants using a molecular marker assay which detects one or more markers linked to the QTLs (and the introgression fragments) for small seed cavity and/or for high dry matter content present in NCIMB 43517 and/or analyzing the fruits of plants grown from said progeny seeds or DH progeny for their average fruit cavity diameter and/or their dry matter content and/or shelf life compared to a control cucumber plant;
- d) identifying and/or selecting a progeny plant comprising: a smaller average fruit cavity diameter and/or an increased dry matter content and/or increased shelf life of the fruit (e.g. when cut) compared to a control cucumber plant.

In step d) the progeny plant identified and/or selected produces fruits that have an average seed cavity diameter of 38% to 47% of the average fruit diameter, and/or the average fruit cavity diameter of the fruits is reduced by at least 3% compared to the variety Hi Power, and/or the fruits, when cut, have a shelf life which is at least 1 or 2 days longer than the shelf life of fruits produced by long cucumber variety Hi Power.

Thus, a method for generating progeny of cucumber variety NUN 09103 CUL is provided, comprising:
- a) growing a plant from seeds deposited under accession number NCIMB 43517;
- b) selfing said plant one or more times or crossing said plant one or more times with another cucumber plant to generate progeny seeds or generating double haploids (DH) from NCIMB 43517 or from said progeny seeds to generate DH progeny;
- c) analyzing the fruits of plants grown from said progeny seeds or DH progeny for their average fruit cavity diameter and/or and/or fruit shelf life compared to long cucumber variety Hi Power; and
- d) identifying and/or selecting a progeny plant that produces fruits that have an average seed cavity diameter of 38% to 47% of the average fruit diameter, and/or the average fruit cavity diameter of the fruits is reduced by at least 3% compared to the variety Hi Power, and/or the fruits, when cut, have a shelf life which is at least 1 or 2 days longer than the shelf life of fruits produced by long cucumber variety Hi Power.

A progeny plant generated by any of the above methods is also an aspect provided herein, as are fruits and fruit parts harvested from any such progeny plants.

DEPOSIT INFORMATION

A representative sample of seeds of a F1 hybrid *Cucumis sativus* var. *sativus* of the long cucumber type, designated cucumber variety NUN 09103 CUL, comprising one or more QTLs conferring a smaller seed cavity size and comprising one or more QTLs conferring an increased dry matter content (reduced moisture leakage and/or reduced moisture content), wherein the QTLs are derived from a short parthenocarpic cucumber donor, and introgressed into a long parthenocarpic cucumber, were deposited by Nunhems B. V. on 18 November 2019 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the deposit number NCIMB 43517. A statement indicating the viability of the sample has been provided.

Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 U.S.C. § 2321 et seq.). Accordingly, the requirements of 37 CFR § 1.801-1.809 have been satisfied.

The following non-limiting Examples describe how one can obtain plants described herein, comprising the QTLs and how one can use one or more of the QTLs in generating cucumber plants making fruits which comprise a small seed cavity and/or an increased dry matter content compared to the control plant lacking the QTLs.

EXAMPLES

Example 1—Material

During the breeding program leading up to the present disclosure a short, parthenocarpic cucumber line which did not have any deviating phenotype from other short cucumber lines, was crossed with a long cucumber line and a BC1 population was made by crossing the F1 obtained from the initial cross back to the long cucumber line. The BC1 population was selfed to produce a BC1S1 population. In the BC1S1 population it was noticed that there were cucumber fruits which deviated in appearance, which had smaller seed cavities and appeared dryer. These two phenotypes appeared to segregate in the BC1S1 population quantitatively.

Plants of the BC1S1 population having a small seed cavity size and high dry matter was selected to make a double haploid population (DH).

One of the DH lines, which had the small seed cavity and high dry matter content was used as a parent line in a cross with an elite long cucumber breeding line to produce an F1 hybrid, which was named NUN 09103 CUL. 2500 seeds of the F1 hybrid were deposited at the NCIMB and received accession number NCIMB 43571.

Example 2—Phenotypic Characterization

Early 2019 seeds of cucumber variety NUN 09103 CUL, Consapino RZ, Hi Power and some other long cucumber hybrids were sown. Hi Power is a high-wire variety, which produces typical long cucumber fruits with a large seed cavity.

About four weeks after sowing, plants were transplanted into the greenhouse and grown in high-wire cultivation. In week 5 of 2019 (when plants had already grown for about four weeks in the greenhouse) four plants of each variety were selected and one representative cucumber fruit was harvested from the stem of each plant. The same was done in week 6, 8, 9, 11 and 15 of 2019.

The following measurements were carried out for all fruits and the average was determined for the four fruits of each variety: fruit weight, fruit length, fruit diameter in the middle of the fruit, cavity diameter in the middle of the fruit.

| NUN 09103 CUL | Week 5 | Week 6 | Week 8 | Week 9 | Week 11 | Week 15 |
|---|---|---|---|---|---|---|
| Average fruit weight (grams) | 431.25 | 408 | 468.75 | 399.25 | 512.5 | 396.75 |
| Average fruit length (cm) | 30 | 32 | 31.25 | 31 | 34.75 | 32.25 |
| Average fruit diameter (mm) | 44.25 | 39.5 | 44.7 | 41.825 | 41.25 | 39.425 |
| Average Fruit cavity Diameter (mm) | 20 | 17.5 | 19.575 | 19.75 | 15.6 | 15.525 |

| Control Hi-Power | Week 5 | Week 6 | Week 8 | Week 9 | Week 11 | Week 15 |
|---|---|---|---|---|---|---|
| Average fruit weight (grams) | 438.25 | 399.25 | 389 | 380 | 400.75 | 366.5 |
| Average fruit length (cm) | 29.5 | 30.5 | 30 | 30.25 | 30.75 | 31.25 |
| Average fruit diameter (mm) | 48 | 42 | 43.5 | 42.65 | 43.125 | 39.6 |
| Average Fruit cavity Diameter (mm) | 24.75 | 20.25 | 21.7 | 21.275 | 22.075 | 19 |

| Consapino RZ | Week 5 | Week 6 | Week 8 | Week 9 | Week 11 | Week 15 |
|---|---|---|---|---|---|---|
| Average fruit weight (grams) | 448.75 | 437 | 401.25 | 290.5 | 364.75 | 347 |
| Average fruit length (cm) | 32.5 | 33 | 32.25 | 29.75 | 33 | 32.75 |

-continued

| Consapino RZ | Week 5 | Week 6 | Week 8 | Week 9 | Week 11 | Week 15 |
|---|---|---|---|---|---|---|
| Average fruit diameter (mm) | 44.5 | 43.25 | 41.925 | 35.35 | 37.75 | 38 |
| Average Fruit cavity Diameter (mm) | 17 | 14.5 | 15.275 | 14.475 | 11.625 | 14.5 |

The average seed cavity diameter was expressed as a percentage of the average fruit diameter, as shown below, and is also shown in FIG. 3.

| | Week 5 | Week 6 | Week 8 | Week 9 | Week 11 | Week 15 | Range of seed cavity diameter percentages of the fruit |
|---|---|---|---|---|---|---|---|
| NUN 09103 CUL | 45% | 44% | 44% | 47% | 38% | 39% | 38% to 47% |
| Hi Power (control) | 52% | 48% | 50% | 50% | 51% | 48% | 48% to 52% |
| Difference between NUN 9103 CUL and the control | 7% | 4% | 6% | 3% | 13% | 9% | Reduction by 3% to 13% |
| Consapino RZ | 38% | 34% | 36% | 41% | 31% | 38% | 31% to 38% |
| Difference between Consapino RZ and the control | 14% | 14% | 14% | 9% | 20% | 10% | Reduction by 9% to 20% |

As can be seen, Hi Power has the largest seed cavity, cucumber variety NUN 09103 CUL had a significantly smaller seed cavity and Consapino RZ had the smallest seed cavity relative to the overall fruit diameter. One or more of the QTLs present in cucumber variety NUN 09103 CUL, therefore, reduce the percentage of seed cavity diameter of the fruit by at least 3% and more.

Fruits of cucumber variety NUN 09103 CUL and of Consapino RZ cut through the middle appeared to be much dryer and leaked less moisture when pressed on with the hand than fruits of Hi Power.

Example 3—Shelf Life Comparison

An experiment was set up to determine the shelf life of freshly cut and packaged cucumber slices of the above varieties. Head and tail of the fruits were removed, and fruits were cut lengthwise into two halves. The halves were separated into two groups, from one group the seed cavity was removed with a knife, from the other group not. The halves were cut into 8 mm thick slices using an SN1000 slicer, resulting in 8 mm thick half-moon slices, either with seed cavity or without seed cavity (see, FIG. 4). After slicing the pieces were washed with ice water and centrifuged to remove surplus water. The slices were placed by hand in a bowl (Fruitschaal deluxe H40) and the bowls were sealed mechanically with foil (PET foil). The packaged slices were then placed into 6° C. in the dark until the evaluation date. Evaluation dates after packaging were after 1 day, after 5 days, after 6 days, after 7 days and after 8 days, indicated as P+1, P+5, etc.

Evaluations were done as follows. The cucumber slices of each package was evaluated for visual appearance (fresh, color), smell (fresh, neutral, not-fresh, sour, rotten), taste (fresh, neutral, sour, bitter, old) and feel (hard, soft, moist, wet). An overall rating was given on the following scale:
2=very bad, 3=bad, 4=insufficient, 5=moderate, 6=sufficient, 7=good, 8=very good.

|  | P + 1 | P + 5 | P + 6 | P + 7 | P + 8 |
|---|---|---|---|---|---|
| NUN 09103 CUL With cavity | 8 | 7.5 | 7.5 (FIG. 4) | 5 | 4 |
| NUN 09103 CUL Without cavity | 8 | 8 | 8 (FIG. 4) | 6 | Not scored |
| Hi-Power With cavity | 8 | 6.5 | 5 (FIG. 4) | 2 | Not scored |
| Hi-Power Without cavity | 8 | 6.5 | 5 (FIG. 4) | 2 | Not scored |
| Consapino RZ With cavity | 8 | 7.5 | 7 | 5 | 4 |
| Consapino RZ Without cavity | 8 | 8 | 8 | 6.5 | 4 |

FIG. 4 shows that cucumber variety NUN 09103 CUL has a better shelf life than the control variety Hi Power. Cut and packaged it can be kept in the fridge at least 1 or 2 days longer. When the seed cavity is removed, shelf life is better than when the seed cavity is still present.

Example 4—Variety Characteristics of Cucumber Variety NUN 09103 CUL

The following are the characteristics of cucumber variety NUN 09103 CUL based on a trial in Acampo, California, USA. Seeding date: Jun. 8, 2020; Transplanting date: Jun. 26, 2020; Harvesting date: Aug. 5, 2020. Tables A and B show the comparison of UPOV test guideline characteristics of cucumber variety NUN 09103 CUL and the Reference Variety, see, world wide web at upov.int/test_guidelines/en/list.jsp, and select the Test Guidelines for cucumber. Table C shows the comparison USDA descriptors of cucumber variety NUN 09103 CUL and the Reference Variety, see, worldwide web at ams.usda.gov/ under services/plant-variety-protection/pvpo-c-forms under cucumber. The Reference Variety used as comparison is Hi Power or NUN 29997 CUL, a commercial variety from Nunhems B.V.

One replication of 30 plants per variety, from which at least 15 plants or plant parts were randomly selected and were used to measure the characteristics. For numerical characteristics, averages were calculated. For non-numerical characteristics, the type/degree were determined. Similarity and differences between two different plant lines or varieties can be determined by comparing the number of morphological and/or physiological characteristics (e.g., characteristics as listed in Tables A-C) that are the same (i.e., statistically not significantly different) or that are different (i.e., statistically significantly different) between two plant lines or varieties using plants grown under the same environmental conditions. A numerical characteristics is considered to be "the same" when the value for a numeric characteristics is not significantly different at the 1% ($p<0.01$) or 5% ($p<0.05\%$) significance level, using T-test, a standard method known to the skilled person. Non-numerical or "degree" or "type" characteristic is considered "the same" when the values have the same "degree" or "type" when scored using USDA and/or UPOV descriptors for plants grown under the same environmental conditions.

TABLE A

Objective Description of Cucumber Variety NUN 09103 CUL and the Reference Variety (UPOV Descriptors)

| Characteristics | Application Variety (NUN 09103 CUL) | Reference Variety (HI POWER) |
|---|---|---|
| Cotyledon: | | |
| Bitterness: Absent, Present | Absent | Absent |
| Stem: | | |
| Stem diameter, mm: | 17.06 mm | 12.47 mm |
| Total length of first 15 internodes: | Medium to long | Medium to long |
| Number of female flowers per node: Predominantly one, Predominantly one or two, Predominantly two, Predominantly two or three, Predominantly three or four, Predominantly four or five, Predominantly more than five | Predominantly one | Predominantly one or two |
| Vigor: Very weak, Weak, Medium, Strong, Very strong | Strong | Very strong |
| Leaf (mature blade): | | |
| Attitude: Erect, Horizontal, Drooping | Drooping | Horizontal |
| Length: Short, Medium, Long | Medium | Medium |
| Ratio of length of terminal lobe/length of blade: Very small, Short, Medium, Large, Very large | Medium | Medium to large |
| Shape of apex of terminal lobe: Acute, Right-angled, Obtuse, Rounded | Obtuse | Acute |
| Intensity of green color: Light, Medium, Dark, Very dark | Medium green | Dark green |

TABLE A-continued

Objective Description of Cucumber Variety NUN 09103 CUL and the Reference Variety (UPOV Descriptors)

| Characteristics | Application Variety (NUN 09103 CUL) | Reference Variety (HI POWER) |
|---|---|---|
| Blistering:<br>Absent or very weak, Weak, Medium, Strong, Very strong | Absent or very weak | Weak |
| Undulation of margin:<br>Absent or very weak, Moderate, Strong | Absent or very weak | Absent or very weak |
| Dentation of margin:<br>Very weak, Weak, Medium, Strong, Very strong | Very weak | Very weak |
| Petiole diameter, mm: | 10.20 mm | 10.14 mm |
| Ovary: | | |
| Color of vestiture:<br>White, Black | White | White |
| Parthenocarpy:<br>Absent, Present | Present | Present |
| Fruit at edible maturity: | | |
| Length:<br>Very short, Very short to short, Short, Short to medium, Medium, Medium to long, Long, Long to very long, Very long | Medium to long | Long |
| Core diameter in relation to diameter of fruit:<br>Very small, Small, Medium, Large, Very large | Small | Medium |
| Core/seed cavity diameter in relation to diameter of fruit:<br>Round, Round to angular, Angular | Round | Round |
| Shape in transverse section:<br>Round, Round to angular, Angular | Round | Round |
| Shape of stem end:<br>Necked, Acute, Obtuse | Acute | Necked |
| Length of neck:<br>Very short, Short, Medium, Long, Very long | Very short | Short |
| Shape of calyx end:<br>Acute, Obtuse, Rounded, Truncate | Obtuse | Obtuse |
| Ground color of skin at market stage:<br>White, Yellow, Green | Green | Green |
| Intensity of ground color of skin at market stage:<br>Very light, Light, Medium, Dark, Very dark | Medium | Medium to dark |
| Ribs:<br>Absent or weak, Medium, Strong | Medium | Absent or weak |
| Sutures:<br>Absent, Present | Absent | Absent |
| Creasing:<br>Absent, Present | Present | Present |
| Degree of creasing:<br>Very weak, Weak, Medium, Strong, Very strong | Medium | Weak to medium |
| Type of vestiture:<br>Hairs only, Hairs and prickles, Prickles only | Prickles only | Prickles only |
| Density of vestiture:<br>Very sparse, Sparse, Medium, Dense, Very dense | Very sparse | Very sparse to sparse |
| Warts:<br>Absent, Present | Absent | Absent |
| Length of stripes:<br>Absent or very short, Short, Medium, Long, Very long | Absent or very short | Absent or very short |
| Dots:<br>Absent, Present | Absent | Absent |
| Glaucosity:<br>Absent or very weak, Weak, Medium, Strong, Very strong | Medium | Very weak to weak |

TABLE A-continued

Objective Description of Cucumber Variety NUN 09103 CUL and the Reference Variety (UPOV Descriptors)

| Characteristics | Application Variety (NUN 09103 CUL) | Reference Variety (HI POWER) |
|---|---|---|
| Ground color of skin at physiological ripeness: White, Yellow, Green, Orange, Brown | Yellow | Yellow |
| Peduncle length, mm: | 76.97 mm | 82.72 mm |
| Peduncle width, mm: | 5.80 mm | 5.34 mm |
| Maturity: | | |
| Time of development of female flowers per node: Very early, Early, Medium, Late, Very late | Early | Early |

TABLE B

Disease Resistances and Other Information of Cucumber Variety NUN 09103 CUL

| Disease resistances | Application Variety (NUN 09103 CUL) | Reference Variety (HI POWER) |
|---|---|---|
| *Cladosporium cucumerinum* | Present | Present |
| Cucumber Mosaic Virus | Susceptible | Susceptible |
| *Etysiphe cichoriacearum* | Not tested | Not tested |
| Powdery mildew (*Podosphaera xanthii*) | Susceptible | Susceptible |
| Downy mildew (*Pseudoperonospora cubensis*) | Not tested | Not tested |
| *Corynespora cassiicola* (*Corynespora* blight and target leaf spot) | Present | Present |
| Papaya Ringspot Virus | Not tested | Not tested |
| Watermelon Mosaic Potyvirus | Not tested | Not tested |
| Cucumber Vein Yellowing Virus | Susceptible | Absent |
| Zucchini Yellow Mosaic Virus | Not tested | Not observed |
| Cucurbit Yellow Stunting Disorder Virus | Absent | Absent |
| Other Information: | | |
| Main use: Processing, Fresh market, Other | Processing; variety with high quality of fruits and good fruit color | Fresh market; variety with high quality of fruits and good fruit color |
| Type of culture: | Greenhouse; indoor cultivation with drip irrigation | Greenhouse; indoor cultivation with drip irrigation |
| Fruit type: | Long type | Long type |

TABLE C

Objective Description of Cucumber Variety NUN 09103 CUL and the Reference Variety (USDA Descriptors)

| Characteristics | Application Variety (NUN 09103 CUL) | Reference Variety (HI POWER) |
|---|---|---|
| Type: | | |
| Predominant usage: Slicing (Fresh Market), Pickling | Processing | Fresh market |
| Predominant Culture: Outdoor, Greenhouse | Greenhouse | Greenhouse |
| Plant: | | |
| Habit: Bush, Semi-bush, Vine | Vine | Vine |
| Growth: Determinate, Indeterminate | Indeterminate | Indeterminate |
| Sex: Andromonoecious, Monoecious, Primarily gynoecious | Gynoecious | Gynoecious |
| Flower color: Yellow, Orange, Green, Other | Yellow | Yellow |
| Main Stem: | | |
| 3$^{rd}$ internode length, cm: | 10.0 cm | 9.84 cm |
| Stem form: | Grooved, ridged | Grooved, ridged |

TABLE C-continued

Objective Description of Cucumber Variety NUN 09103 CUL and the Reference Variety (USDA Descriptors)

| Characteristics | Application Variety (NUN 09103 CUL) | Reference Variety (HI POWER) |
|---|---|---|
| Grooved, ridged; Smooth, round | | |
| Leaf (Mature blade of third leaf): | | |
| Length, mm: | 42.77 mm | 38.13 mm |
| Width, mm: | 39.84 mm | 35.79 mm |
| Petiole length, cm: | 31.55 mm | 23.84 mm |
| Fruit at edible maturity: | | |
| Length, cm: | 30.04 cm | 28.52 cm |
| Diameter at medial, cm: | 4.80 cm | 4.61 cm |
| Weight, gram: | 498.40 g | 393.47 g |
| Skin color: | Not mottled | Not mottled |
| Not mottled, Mottled or speckled with yellow | | |
| Yellowish blossom end stripes: | Absent | Absent |
| Absent, Extend less than ⅓ of the fruit length, Extend more than ⅓ of the fruit length | | |
| Predominant color at stem end: | Dark green | Dark green |
| White, Light Green, Medium Green, Dark Green | (RHS 137A) | (RHS NN137A) |
| Predominant color at blossom end: | Medium green | Medium green |
| White, Light Green, Medium Green, Dark Green | (RHS 137B) | (RHS 144B) |
| Fruit neck shape: | Not necked | Necked |
| Not necked, necked | | |
| Fruit tapering: | Ends blunt or rounded | Stem end tapered |
| Both ends tapered, Stem end tapered, Blossom end tapered, Ends blunt or rounded | | |
| Stem end cross section: | Circular | Circular |
| Circular, Triangular, Square | | |
| Medial cross section: | Circular | Circular |
| Circular, Triangular, Square | | |
| Blossom end cross section: | Triangular | Triangular |
| Circular, Triangular, Square | | |
| Skin Thickness: | Thin | Thin |
| Thick, Thin | | |
| Skin ribs: | Ribbed | Not ribbed |
| Ribbed, Not Ribbed | | |
| Skin luster: | Glossy | Glossy |
| Dull, Glossy | | |
| Spine quality: | Fine | Fine |
| Coarse, Fine | | |
| Spine density: | Absent | Absent |
| Few, Many | | |
| Tubercles (Warts): | Absent | Absent |
| Few, obscure; Many, obscure; Few, prominent; Many, prominent | | |
| Disease resistances: | | |
| *Cladosporium cucumerinum*(Ccu) | Present | Present |
| *Corynespora cassiicola* (*Corynespora* blight and target leaf spot) | Present | Present |

In one aspect, a statistical analysis of the quantitative characteristics showing the degree of significance is provided. For the purpose of proving differences or distinction between cucumber variety NUN 09103 CUL and the Reference Variety, a T-test is used, a statistical tool for proving significance in the means of two groups (e.g., cucumber variety NUN 09103 CUL and the Reference Variety) at 5% significance level (a p-value of 5% or 0.05). The statistical analysis is drawn from a small sample of at least 15 plants or plant parts of cucumber variety NUN 09103 CUL and the Reference Variety. Statistical points or parameters such as mean, minimum, median, maximum, and standard deviation are collected from the sample data to analyze where the average is, how varied the data set is, and whether the data is skewed.

The results of the T-Test show significant differences at 5% significance level between cucumber variety NUN 09103 CUL and the Reference Variety for stem diameter, mature leaf length, mature leaf width, petiole length, mature fruit weight, mature fruit length, and peduncle width as shown in Tables D to J.

Table D shows a significant difference between cucumber variety NUN 09103 CUL and the Reference Variety (p<0.001) for stem diameter (mm) based on a trial conducted in the US during the trial season 2020.

TABLE D

| Statistical Parameter | Application Variety (NUN 09103 CUL) | Reference Variety (Hi Power) |
|---|---|---|
| Number of samples | 15 | 15 |
| Minimum | 13.48 | 10.39 |
| Maximum | 20.45 | 15.78 |
| Median | 17.14 | 12.07 |
| Mean | 17.06 | 12.47 |
| Standard deviation | 2.09 | 1.67 |

Table E shows a significant difference between cucumber variety NUN 09103 CUL and the Reference Variety (p<0.001) for mature leaf length (cm) based on a trial conducted in the US during the trial season 2020.

TABLE E

| Statistical Parameter | Application Variety (NUN 09103 CUL) | Reference Variety (Hi Power) |
|---|---|---|
| Number of samples | 15 | 15 |
| Minimum | 38.30 | 34.10 |
| Maximum | 46.0 | 42.10 |
| Median | 42.80 | 37.60 |
| Mean | 42.77 | 38.13 |
| Standard deviation | 1.83 | 1.96 |

Table F shows a significant difference between cucumber variety NUN 09103 CUL and the Reference Variety (p<0.001) for mature leaf width (cm) based on a trial conducted in the US during the trial season 2020.

TABLE F

| Statistical Parameter | Application Variety (NUN 09103 CUL) | Reference Variety (Hi Power) |
|---|---|---|
| Number of samples | 15 | 15 |
| Minimum | 38.10 | 33.60 |
| Maximum | 41.80 | 42.30 |
| Median | 39.60 | 35.20 |
| Mean | 39.84 | 35.79 |
| Standard deviation | 1.12 | 2.07 |

Table G shows a significant difference between cucumber variety NUN 09103 CUL and the Reference Variety (p<0.001) for petiole length (cm) based on a trial conducted in the US during the trial season 2020.

TABLE G

| Statistical Parameter | Application Variety (NUN 09103 CUL) | Reference Variety (Hi Power) |
|---|---|---|
| Number of samples | 15 | 15 |
| Minimum | 26.80 | 20.90 |
| Maximum | 37.10 | 26.70 |
| Median | 31.30 | 23.80 |
| Mean | 31.55 | 23.84 |
| Standard deviation | 2.78 | 1.58 |

Table H shows a significant difference between cucumber variety NUN 09103 CUL and the Reference Variety (p<0.001) for mature fruit weight (g) based on a trial conducted in the US during the trial season 2020.

TABLE H

| Statistical Parameter | Application Variety (NUN 09103 CUL) | Reference Variety (Hi Power) |
|---|---|---|
| Number of samples | 15 | 15 |
| Minimum | 360.0 | 300.00 |
| Maximum | 718.0 | 510.0 |
| Median | 498.0 | 388.0 |
| Mean | 498.40 | 393.47 |
| Standard deviation | 76.20 | 48.68 |

Table I shows a significant difference between cucumber variety NUN 09103 CUL and the Reference Variety (p=0.003) for mature fruit length (cm) based on a trial conducted in the US during the trial season 2020.

TABLE I

| Statistical Parameter | Application Variety (NUN 09103 CUL) | Reference Variety (Hi Power) |
|---|---|---|
| Number of samples | 15 | 15 |
| Minimum | 28.10 | 27.10 |
| Maximum | 33.30 | 30.80 |
| Median | 29.80 | 28.50 |
| Mean | 30.04 | 28.52 |
| Standard deviation | 1.43 | 1.05 |

Table J shows a significant difference between cucumber variety NUN 09103 CUL and the Reference Variety (p=0.011) for peduncle width (mm) based on a trial conducted in the US during the trial season 2020.

TABLE J

| Statistical Parameter | Application Variety (NUN 09103 CUL) | Reference Variety (Hi Power) |
|---|---|---|
| Number of samples | 15 | 15 |
| Minimum | 4.92 | 4.67 |
| Maximum | 6.57 | 6.15 |
| Median | 5.65 | 5.33 |
| Mean | 5.80 | 5.34 |
| Standard deviation | 0.46 | 0.46 |

The results of the T-Test show no significant difference at 5% significance level between cucumber variety NUN 09103 CUL and the Reference Variety for petiole diameter, mature fruit diameter, 3rd internode length, and peduncle length as shown in Tables K-N.

Table K shows no significant difference between cucumber variety NUN 09103 CUL and the Reference Variety (p=0.870) for petiole diameter (mm) based on a trial conducted in the US during the trial season 2020.

TABLE K

| Statistical Parameter | Application Variety (NUN 09103 CUL) | Reference Variety (Hi Power) |
|---|---|---|
| Number of samples | 15 | 15 |
| Minimum | 7.97 | 8.81 |
| Maximum | 11.72 | 11.98 |
| Median | 10.07 | 10.0 |
| Mean | 10.20 | 10.14 |
| Standard deviation | 1.05 | 0.82 |

Table L shows no significant difference between cucumber variety NUN 09103 CUL and the Reference Variety (p=0.070) for mature fruit diameter (mm) based on a trial conducted in the US during the trial season 2020.

TABLE L

| Statistical Parameter | Application Variety (NUN 09103 CUL) | Reference Variety (Hi Power) |
|---|---|---|
| Number of samples | 15 | 15 |
| Minimum | 4.26 | 4.09 |
| Maximum | 5.53 | 5.09 |
| Median | 4.79 | 4.57 |
| Mean | 4.80 | 4.61 |
| Standard deviation | 0.29 | 0.26 |

Table M shows no significant difference between cucumber variety NUN 09103 CUL and the Reference Variety (p=0.592) for 3rd internode length (cm) based on a trial conducted in the US during the trial season 2020.

TABLE M

| Statistical Parameter | Application Variety (NUN 09103 CUL) | Reference Variety (Hi Power) |
|---|---|---|
| Number of samples | 15 | 15 |
| Minimum | 8.50 | 8.90 |
| Maximum | 11.80 | 11.0 |
| Median | 9.90 | 9.50 |
| Mean | 10.0 | 9.84 |
| Standard deviation | 0.92 | 0.68 |

Table N shows no significant difference between cucumber variety NUN 09103 CUL and the Reference Variety (p=0.062) for peduncle length (mm) based on a trial conducted in the US during the trial season 2020.

TABLE N

| Statistical Parameter | Application Variety (NUN 09103 CUL) | Reference Variety (Hi Power) |
|---|---|---|
| Number of samples | 15 | 15 |
| Minimum | 68.30 | 63.75 |
| Maximum | 88.14 | 96.38 |
| Median | 77.52 | 83.55 |
| Mean | 76.97 | 82.72 |
| Standard deviation | 5.67 | 9.79 |

Another aspect provided herein is cucumber variety NUN 09103 CUL, and its use in producing cucumber fruits for the fresh market or for processed food products (such as slices or dices, packed alone or in combination with other food ingredients, such as lettuce leaves, or on sandwiches).

One aspect is a plant, plant part, or seed of cucumber variety NUN 09103 CUL, wherein a representative sample of seed of said cucumber variety is deposited under Accession Number NCIMB 43517.

One aspect is the plant part above, wherein said plant part is a leaf, pollen, an ovule, a fruit, a scion, a root, a rootstock, a cutting, a flower, or a cell.

Another aspect is a seed that produces the plant variety NUN 09103 CUL above.

A further aspect is a seed grown on the plant of cucumber variety NUN 09103 CUL, wherein a plant grown from said seed does not differ from the plant of cucumber variety NUN 09103 CUL when the numerical characteristics are determined at the 5% significance level and determined by type or degree for non-numerical characteristics when grown under the same environmental conditions.

Furthermore, provided is a cucumber plant having all of the physiological and morphological characteristics of the plant of cucumber variety NUN 09103 CUL, when grown under the same environmental conditions.

Also an aspect is a cucumber plant or a part thereof derived from the plant part above which does not differ from the plant of cucumber variety NUN 09103 CUL in the characteristics listed in Tables A-C, when the numerical characteristics are determined at the 5% significance level and determined by type or degree for non-numerical characteristics when grown under the same environmental conditions, and wherein a representative sample of seed of said cucumber variety is deposited under Accession Number NCIMB 43517.

Furthermore, provided is a tissue or cell culture comprising regenerable cells of the plant of cucumber variety NUN 09103 CUL, said cells being derived from cucumber variety NUN 09103 CUL and suitable for regeneration into a plant having all of the physiological and morphological characteristics of cucumber variety NUN 09103 CUL.

The tissue or cell culture may comprise cells or protoplasts derived from a plant part of cucumber variety NUN 09103 CUL, wherein the plant part is a meristem, a cotyledon, a hypocotyl, pollen, a leaf, an anther, a roots, a root tip, a pistil, a petiole, a flower, a fruit, or a stem.

Another aspect is a cucumber plant regenerated from the tissue or cell culture above, wherein the plant has all of the physiological and morphological characteristics of the plant of variety NUN 09103 CUL, when the characteristics are determined at the 5% significance level and determined by type or degree for non-numerical characteristics for plants grown under the same environmental conditions, and wherein a representative sample of seed of said variety is deposited under Accession Number NCIMB 43517.

A method of producing the plant of cucumber variety NUN 09103 CUL is provided, said method comprising vegetatively propagating at least a part of the plant of variety NUN 09103 CUL, wherein a representative sample of seed of said cucumber variety is deposited under Accession Number NCIMB 43517.

The method herein above is provided, wherein the vegetative propagation comprises regenerating a whole plant from said part of the plant of variety NUN 09103 CUL, wherein a representative sample of seed of said cucumber variety is deposited under Accession Number NCIMB 43517.

In this method said part may be a cutting, a cell culture, or a tissue culture.

Also encompassed herein is a vegetative propagated plant of cucumber variety NUN 09103 CUL, or a part thereof, wherein the vegetative propagated plant has all of the physiological and morphological characteristics of the plant of variety NUN 09103 CUL, when the characteristics are determined at the 5% significance level and determined by type or degree for non-numerical characteristics for plants grown under the same environmental conditions, and wherein a representative sample of seed of said cucumber variety is deposited under Accession Number NCIMB 43517.

Another aspect is a method of producing a cucumber plant, said method comprising crossing the plant above (cucumber variety NUN 09103 CUL) with a second cucumber plant at least once, and selecting a progeny cucumber plant from said crossing and optionally allowing the progeny cucumber plant to form seed. The progeny cucumber plant retains in one aspect the small fruit cavity and/or the high dry matter content, i.e., they retain one or more of the QTLs conferring these characteristics.

Also provided herein is a method of producing of cucumber plants, said method comprising crossing the cucumber plants and harvesting the resultant seed, wherein at least one cucumber plant is cucumber variety NUN 09103 CUL, wherein a representative sample of seed of said cucumber variety is deposited under Accession Number NCIMB 43517.

A first generation progeny plant of the plant cucumber variety NUN 09103 CUL is encompassed, obtained by selfing or cross-pollinating the plant of cucumber variety NUN 09103 CUL with another cucumber plant, wherein said progeny plant has all of the physiological and morphological characteristics of the plant of variety NUN 09103 CUL, when the numerical characteristics are determined at the 5% significance level and determined by type or degree for non-numerical characteristics for plants grown under the same environmental conditions, and wherein a representative sample of seed of said cucumber variety is deposited under Accession Number NCIMB 43517. The progeny cucumber plant retains in one aspect the small fruit cavity and/or the high dry matter content, i.e., they retain one or more of the QTLs conferring these characteristics.

Likewise, a cucumber plant derived from the plant part of cucumber variety NUN 09103 CUL having one physiological or morphological characteristic which is different from those of the plant of cucumber variety NUN 09103 CUL and which otherwise has all the physiological and morphological characteristics of the plant of claim 1, when the numerical characteristics are determined at the 5% significance level and determined by type or degree for non-numerical characteristics for plants grown under the same environmental conditions, and wherein a representative sample of seed of said cucumber variety is deposited under Accession Number NCIMB 43517. The derived cucumber plant retains in one aspect the small fruit cavity and/or the high dry matter content, i.e., they retain one or more of the QTLs conferring these characteristics.

Furthermore, provided is a cucumber plant having all of the physiological and morphological characteristics of the plant of cucumber variety NUN 09103 CUL, when the numerical characteristics are determined at the 5% significance level and determined by type or degree for non-numerical characteristics for plants grown under the same environmental conditions, and wherein a representative sample of seed of said cucumber variety is deposited under Accession Number NCIMB 43517, further comprising a transgene.

In a different aspect, the plant of cucumber variety NUN 09103 CUL is provided, further comprising a single locus conversion, wherein said plant otherwise has all of the physiological and morphological characteristics of cucumber variety NUN 09103 CUL, wherein a representative sample of seed of said cucumber variety is deposited under Accession Number NCIMB 43517, when grown under the same environmental conditions, and wherein the single locus conversion confers male sterility, herbicide tolerance, insect resistance, pest resistance, disease resistance, environmental stress tolerance, modified carbohydrate metabolism, or modified protein metabolism.

A method of making doubled haploids of cucumber variety NUN 09103 CUL, said method comprising making doubled haploid cells from haploid cells of the plant of NUN 09103 CUL, wherein a representative sample of seed of said cucumber variety is deposited under Accession Number NCIMB 43517.

A container comprising the plant, plant part or seed of cucumber variety NUN 09103 CUL is encompassed.

Also a food, a feed product, or a processed product comprising the plant part of cucumber variety NUN 09103 CUL, especially comprising a fruit part, such as a sliced or diced part of the fruit.

A method of producing a cucumber fruit is provided, said method comprising growing plant of cucumber variety NUN 09103 CUL until it sets at least one fruit, and collecting the fruit.

A method of producing a cucumber plant with a desired trait, comprising mutating a plant of variety NUN 09103 CUL and selecting a mutated plant with a desired trait, wherein the mutated plant otherwise retains all of the physiological and morphological characteristics of cucumber variety NUN 09103 CUL, when the numerical characteristics are determined at the 5% significance level for plants and determined by type or degree for non-numerical characteristics grown under the same environmental conditions, wherein a representative sample of seed of said cucumber variety is deposited under Accession Number NCIMB 43517, and wherein the desired trait is male sterility, herbicide tolerance, insect resistance, pest resistance, disease resistance, environmental stress tolerance, modified carbohydrate metabolism, or modified protein metabolism.

In yet another aspect, a method of determining the genotype of cucumber variety NUN 09103 CUL is provided, said method comprising obtaining a sample of nucleic acids from cucumber variety NUN 09103 CUL and detecting in said nucleic acids a plurality of polymorphisms, thereby determining the genotype of the plant and storing the results of detecting the plurality of polymorphisms on a computer readable medium.

The invention claimed is:

1. A plant, plant part, or seed of cucumber variety NUN 09103 CUL, wherein a representative sample of seeds of said variety have been deposited under Accession Number NCIMB 43517.

2. A cucumber fruit produced by the plant according to claim 1.

3. Seed from which the plant according to claim 1 can be grown.

4. The plant part of claim 1, wherein said plant part is a leaf, a fruit, a scion, a root, a rootstock, a cutting, or a flower.

5. A cucumber plant having all of the physiological and morphological characteristics of the plant of claim 1 when grown under the same environmental conditions.

6. A cucumber plant or part thereof derived from the plant of claim 1 which does not differ from the plant of variety NUN 09103 CUL when grown under the same environmental conditions, and wherein a representative sample of seed of said variety has been deposited under Accession Number NCIMB 43517.

7. A tissue or cell culture comprising regenerable cells of the plant of claim 1, said cells being derived from cucumber variety NUN 09103 CUL and suitable for regeneration into a plant having all of the physiological and morphological characteristics of cucumber variety NUN 09103 CUL.

8. The tissue or cell culture according to claim 7, comprising cells or protoplasts derived from a plant part of cucumber variety NUN 09103 CUL, wherein the plant part is a meristem, a cotyledon, a hypocotyl, a leaf, an anther, a root, a root tip, a pistil, a petiole, a flower, a fruit, a stem, or a stalk.

9. A cucumber plant regenerated from the tissue or cell culture of claim 7, wherein the plant has all of the physiological and morphological characteristics of the plant of variety NUN 09103 CUL when grown under the same environmental conditions, and wherein a representative sample of seed of said variety has been deposited under Accession Number NCIMB 43517.

10. A method of producing the plant of claim 1, said method comprising vegetatively propagating at least a part of the plant of variety NUN 09103 CUL, and wherein a representative sample of seed of said variety has been deposited under Accession Number NCIMB 43517.

11. The method of claim 10, wherein the vegetative propagation comprises regenerating a whole plant from said part of the plant of variety NUN 09103 CUL, and wherein a representative sample of seed of said variety has been deposited under Accession Number NCIMB 43517.

12. The method of claim 10, wherein said part is a cutting, a cell culture, or a tissue culture.

13. A vegetatively propagated plant of claim 1, or a part thereof, wherein the vegetative propagated plant has all of the physiological and morphological characteristics of the plant of variety NUN 09103 CUL when grown under the same environmental conditions, and wherein a representative sample of seed of said variety has been deposited under Accession Number NCIMB 43517.

14. A method of producing a cucumber plant, said method comprising crossing the plant of claim 1 with a second cucumber plant at least once, and selecting a progeny cucumber plant from said crossing and optionally allowing the progeny to form seed.

15. A method of making doubled haploids of cucumber variety NUN 09103 CUL, said method comprising making doubled haploid cells from haploid cells of cucumber variety NUN 09103 CUL, wherein a representative sample of seed of said variety has been deposited under Accession Number NCIMB 43517.

16. A container comprising the plant, plant part, or seed of claim 1.

17. A food, a feed product, or a processed product comprising the plant part of claim 4, wherein the plant part comprises at least a cell of cucumber variety NUN 09103 CUL.

18. A method of producing a cucumber fruit, said method comprising growing the plant of claim 1 until it sets at least one fruit and collecting the fruit.

19. A fruit produced by the method of claim 18.

20. A plant of cucumber variety NUN 09103 CUL, further comprising a single locus conversion, wherein the single locus converted plant otherwise has all of the morphological and physiological characteristics of the plant of variety NUN 09103 CUL when grown under the same environmental conditions, and wherein a representative sample of seed of said variety has been deposited under Accession Number NCIMB 43517, optionally wherein the single locus conversion confers male sterility, herbicide tolerance, insect resistance, pest resistance, disease resistance, environmental stress tolerance, modified carbohydrate metabolism, or modified protein metabolism.

21. A method of producing a cucumber plant with a desired trait, said method comprising mutating the plant of cucumber variety NUN 09103 CUL and selecting a mutated plant with a desired trait, wherein the mutated plant otherwise retains all of the physiological and morphological characteristics of the plant of cucumber variety NUN 09103 CUL when grown under the same environmental conditions, wherein a representative sample of seed of cucumber variety NUN 09103 CUL has been deposited under Accession Number NCIMB 43517, and wherein the desired trait is male sterility, herbicide tolerance, insect resistance, pest resistance, disease resistance, environmental stress tolerance, modified carbohydrate metabolism, or modified protein metabolism.

22. A method of producing a cucumber plant, said method crossing cucumber plants and harvesting the resultant seed, wherein at least one cucumber plant is the plant of claim 1, wherein a representative sample of seed of cucumber variety NUN 09103 CUL has been deposited under Accession Number NCIMB 43517.

23. A method of determining the genotype of the plant of claim 1, said method comprising obtaining a sample of nucleic acids from said plant and detecting in said nucleic acids a plurality of polymorphisms, thereby determining the genotype of the plant and storing the results of detecting the plurality of polymorphisms on a computer readable medium.

24. A method for generating progeny of cucumber variety NUN 09103 CUL, said method comprising:
  a. growing a plant from seeds deposited under Accession Number NCIMB 43517;
  b. selfing said plant one or more times or crossing said plant one or more times with another cucumber plant to generate progeny seeds or generating double haploid (DH) lines from cucumber variety NUN 09103 CUL to generate DH progeny;
  c. analyzing the fruits of plants grown from said progeny seeds or DH progeny for their average fruit seed cavity diameter and/or fruit shelf life compared to long cucumber variety Hi Power; and
  d. identifying and/or selecting a progeny plant that produces fruits that have an average fruit seed cavity diameter of 38% to 47% of the total fruit diameter, and/or the average fruit seed cavity diameter of the fruits is reduced by at least 3% compared to the variety Hi Power, and/or the fruits, when cut, have a shelf life which is at least 1 or 2 days longer than the shelf life of fruits produced by long cucumber variety Hi Power.

* * * * *